US008012117B2

(12) United States Patent
Bonnette et al.

(10) Patent No.: US 8,012,117 B2
(45) Date of Patent: Sep. 6, 2011

(54) MINIATURE FLEXIBLE THROMBECTOMY CATHETER

(75) Inventors: Michael J. Bonnette, Minneapolis, MN (US); Eric J. Thor, Arden Hills, MN (US); Debra M. Kozak, Forest Lake, MN (US); David B. Morris, Anoka, MN (US); John L. Teschendorf, Lino Lakes, MN (US); Douglas J. Ball, Coon Rapids, MN (US); Stephen E. Weisel, Brook Park, MN (US)

(73) Assignee: Medrad, Inc., Indianola, PA (US)

( * ) Notice: Subject to any disclaimer, the term of this patent is extended or adjusted under 35 U.S.C. 154(b) by 0 days.

(21) Appl. No.: 11/702,990

(22) Filed: Feb. 6, 2007

(65) Prior Publication Data
US 2008/0188831 A1 Aug. 7, 2008

(51) Int. Cl.
*A61M 1/00* (2006.01)
*A61B 17/20* (2006.01)

(52) U.S. Cl. .......................................... 604/22; 604/35

(58) Field of Classification Search ............ 604/83–184, 604/22, 35, 43; 428/672
See application file for complete search history.

(56) References Cited

U.S. PATENT DOCUMENTS

| | | | |
|---|---|---|---|
| 1,902,418 A | | 3/1933 | Pilgrim |
| 1,904,241 A | * | 4/1933 | Kammerer ................... 428/656 |
| 3,752,617 A | | 8/1973 | Burlis et al. |
| 3,930,505 A | | 1/1976 | Wallach |
| 4,224,943 A | | 9/1980 | Johnson et al. |
| 4,248,234 A | | 2/1981 | Assenza et al. |
| 4,290,428 A | | 9/1981 | Durand |
| 4,328,811 A | | 5/1982 | Fogarty |
| 4,385,635 A | | 5/1983 | Ruiz |
| 4,495,255 A | * | 1/1985 | Draper et al. ................. 428/669 |
| 4,631,052 A | | 12/1986 | Kensey |
| 4,636,346 A | | 1/1987 | Gold et al. |
| 4,690,672 A | | 9/1987 | Veltrup |
| 4,739,768 A | | 4/1988 | Engelson |
| 4,747,405 A | | 5/1988 | Leckrone |
| 4,775,371 A | | 10/1988 | Mueller, Jr. |
| 4,781,186 A | | 11/1988 | Simpson et al. |
| 4,782,834 A | | 11/1988 | Maguire et al. |
| 4,790,813 A | | 12/1988 | Kensey |
| 4,842,579 A | | 6/1989 | Shiber |
| 4,861,336 A | | 8/1989 | Helzel |
| 4,883,459 A | | 11/1989 | Calderon |

(Continued)

FOREIGN PATENT DOCUMENTS

DE 3705339 9/1988

(Continued)

OTHER PUBLICATIONS

U.S. Appl. No. 09/356,783, "Rheolytic Thrombectomy Catheter and Method of Using Same", Morris et al., filed Jul. 16, 1999.
International Search Report in corresponding application PCT/US02/17617.
European Search Report in corresponding application EP 03253576.7.
European Search Report in corresponding application EP 99308120.
Material Data Sheet for Dow, Calibre MegaRad 2080 10; Polycarbonate, Gamma Radiation Resistant (date unknown).

(Continued)

*Primary Examiner* — Kevin C Sirmons
*Assistant Examiner* — Bradley J Osinski
(74) *Attorney, Agent, or Firm* — David Schramm

(57) ABSTRACT

The present invention pertains to a miniature flexible thrombectomy catheter having one or more flexible miniature non-collapsing tubular portions including pushable and torqueable structure for introduction into the smaller vessels in neurovascular regions. A jet body having an arcuate fluid jet emanator is incorporated in order to minimize size at the distal portion of a minimally sized catheter tube.

22 Claims, 23 Drawing Sheets

U.S. PATENT DOCUMENTS

| | | | |
|---|---|---|---|
| 4,888,146 A | 12/1989 | Dandeneau | |
| 4,898,574 A | 2/1990 | Uchiyama et al. | |
| 4,898,591 A | 2/1990 | Jang et al. | |
| 4,902,276 A | 2/1990 | Zakko | |
| 4,913,698 A | 4/1990 | Ito et al. | |
| 4,950,238 A | 8/1990 | Sullivan | |
| 5,011,469 A | 4/1991 | Buckberg | |
| 5,085,649 A | 2/1992 | Flynn | |
| 5,086,842 A | 2/1992 | Cholet | |
| 5,092,873 A | 3/1992 | Simpson et al. | |
| 5,114,399 A | 5/1992 | Kovalcheck | |
| 5,135,482 A | 8/1992 | Neracher | |
| 5,163,431 A | 11/1992 | Griep | |
| 5,215,614 A | 6/1993 | Wijkamp | |
| 5,221,270 A | 6/1993 | Parker | |
| 5,234,416 A | 8/1993 | Macaulay et al. | |
| 5,250,059 A | 10/1993 | Andreas et al. | |
| 5,254,107 A | 10/1993 | Soltesz | |
| 5,259,842 A | 11/1993 | Plechinger et al. | |
| 5,273,526 A | 12/1993 | Dance et al. | |
| 5,300,022 A | 4/1994 | Klapper et al. | |
| 5,308,342 A | 5/1994 | Sepetka et al. | |
| 5,318,518 A | 6/1994 | Plechinger et al. | |
| 5,320,599 A | 6/1994 | Griep et al. | |
| 5,324,285 A | 6/1994 | Cannon | |
| 5,342,386 A | 8/1994 | Trotta | |
| 5,358,485 A | 10/1994 | Vance et al. | |
| 5,366,464 A | 11/1994 | Belknap | |
| 5,370,609 A | 12/1994 | Drasler et al. | |
| 5,372,601 A | 12/1994 | Lary | |
| 5,380,307 A | 1/1995 | Chee et al. | |
| 5,399,164 A | 3/1995 | Snoke et al. | |
| 5,425,723 A | 6/1995 | Wang | |
| 5,456,674 A | 10/1995 | Bos et al. | |
| 5,478,330 A | 12/1995 | Imran et al. | |
| 5,496,267 A | 3/1996 | Drasler et al. | |
| 5,496,294 A | 3/1996 | Hergenrother et al. | |
| 5,499,973 A | 3/1996 | Saab | |
| 5,531,685 A | 7/1996 | Hemmer et al. | |
| 5,536,242 A | 7/1996 | Willard et al. | |
| 5,542,924 A | 8/1996 | Snoke et al. | |
| 5,554,114 A | 9/1996 | Wallace | |
| 5,554,121 A | 9/1996 | Ainsworth et al. | |
| 5,571,094 A | 11/1996 | Sirhan | |
| 5,599,325 A | 2/1997 | Ju et al. | |
| 5,624,397 A | 4/1997 | Snoke et al. | |
| 5,634,897 A | 6/1997 | Dance et al. | |
| 5,658,263 A | 8/1997 | Dang et al. | |
| 5,662,622 A | 9/1997 | Gore et al. | |
| 5,676,659 A | 10/1997 | McGurk | |
| 5,681,336 A | 10/1997 | Clement et al. | |
| 5,683,345 A | 11/1997 | Waksman et al. | |
| 5,687,714 A | 11/1997 | Kolobow et al. | |
| 5,702,439 A | 12/1997 | Euteneuer et al. | |
| 5,704,926 A | 1/1998 | Sutton | |
| 5,713,849 A | 2/1998 | Bosma et al. | |
| 5,785,675 A | 7/1998 | Drasler et al. | |
| 5,792,167 A | 8/1998 | Kablik et al. | |
| 5,902,266 A | 5/1999 | Leone | |
| 5,928,186 A | 7/1999 | Homsma et al. | |
| 5,944,686 A | 8/1999 | Patterson et al. | |
| 5,964,223 A | 10/1999 | Baran | |
| 5,976,120 A | 11/1999 | Chow et al. | |
| 5,989,210 A | 11/1999 | Morris et al. | |
| 5,989,271 A | 11/1999 | Bonnette et al. | |
| 5,997,558 A | 12/1999 | Nash | |
| 6,001,078 A | 12/1999 | Reekers | |
| 6,022,336 A | 2/2000 | Zadno-Azizi et al. | |
| 6,024,729 A | 2/2000 | Dehdashtian et al. | |
| 6,030,369 A | 2/2000 | Engelson et al. | |
| 6,045,547 A | 4/2000 | Ren et al. | |
| 6,063,069 A | 5/2000 | Cragg et al. | |
| 6,096,001 A | 8/2000 | Drasler et al. | |
| 6,117,150 A | 9/2000 | Pingleton et al. | |
| 6,128,799 A | 10/2000 | Nagata et al. | |
| 6,129,697 A | 10/2000 | Drasler et al. | |
| 6,129,698 A | 10/2000 | Beck | |
| 6,135,977 A | 10/2000 | Drasler et al. | |
| 6,224,570 B1 | 5/2001 | Le et al. | |
| 6,258,061 B1 | 7/2001 | Drasler et al. | |
| 6,287,280 B1 | 9/2001 | Lampropoulos et al. | |
| 6,331,176 B1 | 12/2001 | Becker et al. | |
| 6,355,027 B1 | 3/2002 | Le et al. | |
| 6,357,635 B1 | 3/2002 | Pagliaro et al. | |
| 6,375,635 B1 | 4/2002 | Moutafis et al. | |
| 6,409,863 B1 | 6/2002 | Prindle et al. | |
| 6,414,420 B1 | 7/2002 | Suzuki | |
| 6,420,205 B1 | 7/2002 | Sawai | |
| 6,471,683 B2 | 10/2002 | Drasler et al. | |
| 6,540,734 B1 | 4/2003 | Chiu | |
| 6,544,209 B1 | 4/2003 | Drasler et al. | |
| 6,544,215 B1 * | 4/2003 | Bencini et al. | 604/95.01 |
| 6,558,366 B1 | 5/2003 | Drasler et al. | |
| 6,592,549 B2 | 7/2003 | Gerdts et al. | |
| 6,635,070 B2 | 10/2003 | Leeflang et al. | |
| 6,659,329 B1 | 12/2003 | Hall | |
| 6,676,627 B1 | 1/2004 | Bonnette et al. | |
| 6,676,637 B1 | 1/2004 | Bonnette et al. | |
| 6,719,718 B2 | 4/2004 | Bonnette et al. | |
| 6,730,037 B2 | 5/2004 | Jang | |
| 6,755,803 B1 * | 6/2004 | Le et al. | 604/22 |
| 6,764,483 B1 | 7/2004 | Bonnette et al. | |
| 6,805,684 B2 | 10/2004 | Bonnette et al. | |
| 6,875,193 B1 * | 4/2005 | Bonnette et al. | 604/22 |
| 6,875,949 B2 | 4/2005 | Hall | |
| 6,921,396 B1 | 7/2005 | Wilson | |
| 6,926,726 B2 | 8/2005 | Drasler et al. | |
| 6,945,951 B1 * | 9/2005 | Bonnette et al. | 604/22 |
| 6,964,657 B2 | 11/2005 | Cragg | |
| 6,984,239 B1 | 1/2006 | Drasler et al. | |
| 7,120,992 B2 | 10/2006 | He | |
| 7,179,291 B2 * | 2/2007 | Rourke et al. | 623/2.36 |
| 7,226,433 B2 | 6/2007 | Bonnette et al. | |
| 2001/0051785 A1 | 12/2001 | Bonnette et al. | |
| 2002/0103530 A1 | 8/2002 | You | |
| 2003/0127620 A1 | 7/2003 | Houde | |
| 2004/0068248 A1 | 4/2004 | Mooney et al. | |
| 2004/0116831 A1 | 6/2004 | Vrba | |
| 2004/0133264 A1 * | 7/2004 | Moore | 623/1.12 |
| 2004/0143312 A1 * | 7/2004 | Samson et al. | 607/105 |
| 2005/0059957 A1 * | 3/2005 | Campbell et al. | 604/524 |
| 2005/0142377 A1 | 6/2005 | Hall | |
| 2005/0267408 A1 | 12/2005 | Grandt et al. | |
| 2006/0047223 A1 | 3/2006 | Grandfield et al. | |
| 2006/0064123 A1 | 3/2006 | Bonnette et al. | |

FOREIGN PATENT DOCUMENTS

| | | |
|---|---|---|
| DE | 3421390 | 6/1994 |
| EP | 0251512 | 1/1988 |
| EP | 0232678 | 8/1992 |
| EP | 0528181 | 2/1993 |
| EP | 1382366 | 1/2004 |
| GB | 1571459 | 7/1980 |
| WO | WO9005493 | 5/1990 |
| WO | WO9410917 | 5/1994 |

OTHER PUBLICATIONS

International Search Report for corresponding application PCT/US08/00538.
International Search Report for corresponding application PCT/US08/01515.
International Search Report for corresponding application PCT/US08/01517.
U.S. Appl. No. 12/174,125, "Method of Manufacturing a Miniature Flexible Thrombectomy Catheter".
European Search Report for corresponding application EP 99300846.
International Search Report for corresponding application PCT/US05/41412.
Office Action dated Nov. 18, 2009 in related U.S. Appl. No. 11/096,592.

* cited by examiner

MINIATURE FLEXIBLE THROMBECTOMY CATHETER

CROSS REFERENCES TO RELATED APPLICATIONS

This patent application is related to application Ser. No. 10/455,096 entitled "Thrombectomy Catheter Device with Self-Sealing Hemostasis Valve" filed on Jun. 5, 2003, which is pending; and is related to application Ser. No. 11/096,592 entitled "Rapid Exchange Fluid Jet Thrombectomy Device and Method" filed on Apr. 1, 2005, which is pending; both of which are continuations-in-part of application Ser. No. 10/198,264 entitled "Rapid Exchange Fluid Jet Thrombectomy Device and Method" filed on Jul. 16, 2002, now U.S. Pat. No. 6,875,193; which is a continuation-in-part of application Ser. No. 09/888,455 entitled "Single Operator Exchange Fluid Jet Thrombectomy Device" filed Jun. 25, 2001, now U.S. Pat. No. 6,755,803; which is a continuation-in-part of application Ser. No. 09/356,783 entitled "Rheolytic Thrombectomy Catheter and Method of Using Same" filed Jul. 17, 1999, now abandoned; which is a division of application Ser. No. 09/019,728 entitled "Rheolytic Thrombectomy Catheter and Method of Using Same" filed Feb. 6, 1998, now U.S. Pat. No. 5,989,210.

BACKGROUND OF THE INVENTION

1. Field of the Invention

The present invention is for a thrombectomy catheter device, in general, and more particularly, to a thrombectomy catheter device incorporating a miniature distal portion for introduction into the smaller vessels in neurovascular regions.

2. Description of the Prior Art

Prior art thrombectomy catheters have been designed to access and treat neurological anatomy, whereby the catheter was delivered in two parts. First, a microcatheter was delivered to the site over a guidewire. A microcatheter is essentially a tube which functions as the effluent lumen of the thrombectomy catheter. Then, a nitinol jet body, the part of the thrombectomy catheter that delivers saline to the distal end of the catheter, is delivered inside the microcatheter to the treatment site. The jet body has proximally directed small holes that are partly responsible for the high back pressures developed by the catheter. The holes are positioned to direct high speed jets proximally within the catheter body. In previous neurological thrombectomy catheters, the jet body was designed to include a short skirt. When the jet body was activated by pumped saline, recovered pressures within the catheter assembly would expand the skirt such that the two parts became a unified single catheter assembly. The sequential exchange of devices meant that no guidewire was in place once the jet body was delivered. Hence, there was more lumen capacity for exhaust flow and the catheter size could be kept smaller. This two-part configuration for delivery was difficult to accomplish. Some microcatheters would actually stretch while the jet body was advanced through the lumen. Hence, the jet body was never exposed to enable activation. Sometimes the microcatheter would ovalize in tortuous anatomy making it difficult to deliver the jet body through its lumen. Furthermore, interventionalists are never comfortable giving up their wire position, so removing the wire and exchanging it for a jet body was regarded as a bit awkward and nonintuitive. Prior neurologic thrombectomy catheters were also underpowered for the tough thrombus that is found in embolic stroke patients (organized thrombus from the left atrium). With any given style catheter design there is a trade-off between the thrombectomy power of the catheter and the vessel safety of that catheter design as the neurological arteries are highly fragile (very thin and unsupported vessel walls) and the clot material is tough and organized.

SUMMARY OF THE INVENTION

The general purpose of the present invention is to provide a miniature flexible thrombectomy catheter. A jet body having an arcuate fluid jet emanator is incorporated in order to minimize size at the distal portion of a minimally sized catheter tube.

According to one embodiment of one form of the present invention, there is provided a miniature flexible thrombectomy catheter useful in over-the-wire application. This embodiment includes a manifold and associated components of the manifold, a configured catheter tube extending from the manifold consisting of a proximal flexible tube section joined and connected to a multiple radius flexible distal tube comprised of a proximal section continuous with a smaller distal section, a plurality of outflow orifices and inflow orifices spaced about the periphery of the smaller distal section, and a flexible tip located at the end of the smaller distal section. The smaller distal section is 3 Fr (as measured with reference to the French catheter scale), for purpose of example and demonstration, and is suitably sized for navigation along narrow, restrictive and tortuous paths of the vasculature. The miniature flexible thrombectomy catheter also includes a jet body which is accommodated by the manifold and the configured catheter tube. The minimally dimensioned jet body is comprised of connected tubular components consisting of a flexible proximal high pressure tube, a flexible nitinol tube which functions as a high pressure tube, and a smaller flexible distal high pressure tube having a continuous arcuate fluid jet emanator at the distal end thereof. A unique laser swaging process is used to produce a suitable joint to connect the proximal end of the smaller flexible distal high pressure tube having a continuous arcuate fluid jet emanator to the distal end of the flexible nitinol tube which maintains flexibility, whereas prior art jet body devices incorporated welding techniques to join nitinol tubes to stainless steel tubes resulting in joint brittleness which were subject to failure. A distally located support ring in conjunction with a marker band serves as a support for the arcuate fluid jet emanator which is suitably and supportively secured thereto. A proximally located support ring of nitinol is welded to the flexible nitinol tube and fastened to the small profile distal section of the multiple radius flexible distal tube in cooperation with a marker band for support and positioning of the jet body. The uniquely formed small jet body can also be utilized in other forms of the present invention.

The present invention is able to deliver a catheter tube through a highly tortuous anatomy to the site of thrombus and the like due to the use of flexible and miniaturized components. One key to deliverability is to retain the elastic properties of the various catheter components including and involving both the catheter tube and the jet body contained within the catheter tube. Prior art versions of a neurologic catheter accomplished deliverability by using a lengthy and expensive nitinol jet body. The present invention incorporates a jet body having a short nitinol component in combination with other flexible tubular components to provide for pushable yet flexible deliverability into narrow and tortuous vascular regions. Nitinol is flexible and retains its elastic properties when subjected to severe bending. For example, consider an S-shaped curve. As the thrombectomy catheter negotiates an S-shaped curve, the catheter components will bend. In the case of prior versions of thrombectomy catheters, the jet body (annealed stainless steel hypotubing) will bend plastically (plastic deformation relates to retaining a bent shape). In general, the catheter can make the first bend, but then locks up as it is advanced, since the catheter cannot easily change from one curve at the bottom of the S-curve to a different curve at the top of the S-curve. Accordingly, a nitinol portion of the jet body at the distal end of the catheter will attempt to return to its original shape and not take on a set. This is a necessary design element for this miniature flexible thrombectomy catheter, the present invention. Nitinol is not inexpensive, so the jet body uses a proximal high pressure tube of stainless steel for most of the proximal length of the catheter. The proximal portion of the catheter and the jet body is generally designed to be stiff and is not subjected to much bending. Thus, the stainless steel provides good pushability for the proximal portion of the jet body. In the case of prior art neurological catheters, stepped nitinol was used whereby the proximal end of the jet body had larger diameter nitinol stepping down to smaller diameter nitinol in the distal jet body end of the catheter to provide the desired flexibility. The use of long lengths of nitinol is not economically desirable, whereas attaching a stainless steel tube to a short piece of nitinol tube makes the expense more acceptable. Additionally, the use of stainless steel tubing is desirable in that the pushability of stainless steel tubing is better than that of nitinol tubing.

Another aspect of the forms of the present invention is that cross stream technology is incorporated rather than the other designs used for previous neurologic thrombectomy catheters. Cross stream technology, which uses inflow and outflow windows rather than a circumferential gap, has been shown to have much greater thrombectomy efficacy assuming comparable designs in terms of equivalent vessel safety. Hence, these two approaches of stepping the catheter tube diameter and the use of cross stream technology are the strategies to maximize thrombectomy action of the small profile device.

Another form of the present invention includes incorporating the common jet body into use with a rapid exchange style catheter. This form is closely related to one or more referenced patent applications where a guidewire tube for accommodation of a guidewire extends from the distal tip of the catheter tube to a guidewire tube exit region located along the catheter tube, whereby only a portion of the catheter tube is used for accommodation of a guidewire. This form also relates to a rapid exchange catheter including the use of a substantially full, but interrupted, spiral catheter tube consisting of a proximal tube of spiral cut stainless steel, a short intermediate flexible intermediate tube comprising a guidewire tube exit region thereabout and a distal tube of spiral cut stainless steel. The use of spiral cut catheter tubes enables a varying pitch to be cut into the stainless steel tubing. By introducing a coarse pitch to a fine pitch variation, the stiffness of the full spiral catheter tube can be controlled such that the spiral cut stainless steel proximal tube is relatively stiff at the proximal end and extremely flexible at the distal end. Another pertinent aspect of the full spiral catheter tube is the efficiently designed effluent lumen of the catheter tube. Placing a spiral cut in the stainless steel tubing avoids the plastic deformation issues and provides coils which will bend easily and which can be pushed along its longitudinal axis. The use of spiral cut tubing for the effluent lumen provides for extreme flexibility while retaining pushability through the vasculature, while minimizing the wall thickness of the catheter tube. Furthermore, varying the pitch of the spiral cuts results in differences in flexibility, whereby the proximal sections are purposely made to be stiffer than the flexible distal sections. The spiral cut tubing is jacketed with polymer shrink tubing, or in the alternative, is jacketed by a polymer tube drawn down over the spiral tubing to retain fluid within the spiral cut stainless steel catheter tubes. This polymer jacket is thin and the stainless steel tubing is very thin walled as well to retain most of the flexibility. Consequently, the result of this composite tubing is a thin walled, small diameter, pushable, flexible tube which is the goal of many interventional devices.

In addition, the inflow and outflow orifices are cut into the stainless steel in the full spiral catheter tube eliminating the need for saddles which are conventionally welded to the jet body to support the catheter tube and included lumen in cross stream catheters to prevent inflow and outflow orifice deformation. Normally, saddles or support rings provide structural support for attachment of plastic tubing, but stiffens the catheter tube in this region. The jet body of the present invention can be welded directly to the inside of the full spiral catheter tube. One additional advantage to laser cutting the stainless steel tubing comprising the full spiral catheter tube is that the inflow and outflow orifices can be cut at the same time. By cutting the inflow and outflow orifices directly into the stainless steel, there is no need for saddles, as the inflow and outflow orifices will not deform. This removes a flow restriction for the waste flow and enhances flexibility of the tip of the catheter.

In general, multiple forms of the miniature flexible thrombectomy catheter include common significant aspects and features as applied to all forms of the present invention:

One significant aspect and feature of the present invention is a miniature flexible thrombectomy catheter which can be operated by one practitioner.

Another significant aspect and feature of the miniature flexible thrombectomy catheter is a device of such size, flexibility and construction as to enable ready passage through the small, narrow and tortuous pathways found in the fragile vessels of the heart, the brain, or other body areas, including the more fragile veins.

Another significant aspect and feature of the miniature flexible thrombectomy catheter is a distal portion having a small diameter, such as 3 Fr or smaller, for purposes of example and illustration.

Another significant aspect and feature of the present invention is the use of an arcuate fluid jet emanator, whereby internal catheter tube space is gained for passage of a guidewire.

Another significant aspect and feature of the present invention is the use of a jet body which is accommodated by a manifold and a configured catheter tube, whereby the minimally dimensioned jet body is comprised of connected tubular components consisting of a flexible proximal high pressure tube, a flexible nitinol tube, and a smaller flexible distal high pressure tube having an arcuate fluid jet emanator at the distal end thereof.

Another significant aspect and feature of the present invention is the use of a unique laser swaging process to produce a suitable joint to overlappingly connect the proximal end of the smaller flexible distal high pressure tube which bears the distally located arcuate fluid jet emanator to the distal end of the flexible nitinol tube.

Another significant aspect and feature of the present invention is the use of a unique laser swaging process for gold plating at least the external proximal surface of the smaller flexible distal high pressure tube, which bears the continuously formed and distally located arcuate fluid jet emanator, inserting the gold plated proximal surface of such smaller flexible distal high pressure tube into the distal end of the flexible nitinol tube and directing a laser weld thereabout to form a suitable overlapping joint between the proximal end of the smaller flexible distal high pressure tube and the distal end of the flexible nitinol tube.

Another significant aspect and feature of the present invention is a unique swaging process where suitable temperature heat is applied to a junction having a nitinol tube surrounding a gold plated stainless steel tube. The nitinol tube has a lower melting point than the gold plating of the stainless steel tube. Heat is carefully and appropriately applied to the junction in order to cause the nitinol tube to become soft and elastic, but not to reach the melting point of the gold plating, thereby allowing the nitinol tube to swagingly bond to the gold plating of the stainless steel tube without forming any undesirable gaps.

Another significant aspect and feature of the present invention is the provision of a miniature flexible thrombectomy catheter for producing one or more jets of saline and projecting them in a proximal direction to create a vacuum near the site of thrombus or other unwanted material while pressurizing the exhaust passage.

Still another significant aspect and feature of the present invention is to provide an improved method of removing thrombus or other unwanted material from an obstructed body vessel.

Still another significant aspect and feature of the present invention is a miniature flexible thrombectomy catheter having inflow orifices and outflow orifices to create one or more cross stream jets for enhanced removal of thrombus or other unwanted material.

A further significant aspect and feature of such a form of the present invention is the use of tubular components comprised of materials which provide and promote pushability and torqueability and which provide and promote operator feel.

Another significant aspect and feature of the present invention is the inclusion of structural members which allow minimizing the outer diameter of the device while maximizing the inner diameter of the device. The outer diameter of the device is minimized to provide the least intrusive profile and the inside diameter of the device is maximized for higher and less restrictive exhaust flow.

A yet further significant aspect and feature of the present invention is coating the device hydrophilically for improved movement inside a guide catheter or vessel wall, as well as improved trackability.

A still further significant aspect and feature of the present invention is the ability to incorporate various fluid jet emanator shapes, styles and designs.

An additional significant aspect and feature of the present invention is the reduction of fabrication costs by eliminating complicated extruded shapes, minimizing the number of components, reducing the complexity of the components, and improving the quality of the components.

Another significant aspect and feature of the present invention is a manifold which reduces the number of components and provides superior sealability and bond strengths.

The above listed common significant aspects and features are included with reference to one form of the miniature flexible thrombectomy catheter incorporated into use in over-the-wire applications having additional significant aspects and features, wherein:

One significant aspect and feature of the present invention is the use of a configured catheter tube extending from the manifold consisting of a proximal flexible tube section, preferably of braided polyimide, joined and connected to a multiple radius flexible distal tube, preferably of Pebax, comprised of a proximal section continuous with a smaller distal section, a plurality of outflow orifices and inflow orifices spaced about the distal periphery of the smaller distal section, and a flexible tip located at the end of the smaller distal section.

Another significant aspect and feature of the present invention is the spacing of inflow (and outflow) orifices at 120°, for the purpose of example and illustration, with respect to each other, whereby sufficient tubular catheter tube material included therebetween provides for robust structure between each inflow (and outflow) orifice, thereby minimizing the possibility of collapsing the tubular catheter tube material thereabouts.

Another significant aspect and feature of the present invention is the use of a catheter tube, including the use of materials, such as, but not limited to, braided polyimide, Pebax, and the like, and including a polymer-jacketed covering to provide superior pushability and trackability with a minimal wall thickness and to provide superior handling characteristics while maintaining the smallest wall thickness possible, thereby providing devices of smaller cross section.

Previously mentioned listed common significant aspects and features in paragraphs are included with reference to another form of the miniature flexible thrombectomy catheter incorporated into use in rapid exchange thrombectomy applications having additional significant aspects and features wherein:

Another significant aspect and feature of the present invention is a guidewire tube for passage of a guidewire through the distal portion of the miniature flexible thrombectomy catheter.

Yet another significant aspect and feature of the present invention is a catheter tube having an intermediate tube to provide connection between a proximal spiral metal tube, a distal spiral metal tube, and the guidewire tube at a guidewire exit region.

A still further significant aspect and feature of the present invention is to provide an efficient, reliable, and less costly method of fabricating a rapid exchange catheter by utilizing an intermediate tube formed with a truncated and rounded slot at a guidewire tube exit region.

Another significant aspect and feature of the present invention is the use of a catheter tube having connected spiral metal tubes and an interceding intermediate tube having a polymer-jacketed covering to provide superior pushability and trackability with a minimal wall thickness and to provide superior handling characteristics while maintaining the smallest wall thickness possible, thereby providing devices of smaller cross section.

Another significant aspect and feature of the present invention is the use of spiral metal tubes and a short intermediate tube having a polymer-jacket covering where the combined and connected tubes substantially form a spiral interrupted only by the short intermediate tube which may occur in groups of constant pitch or in progressive pitch as appropriate along the length of the catheter tube to provide a continuous or other pitch transition.

Another significant aspect and feature of the present invention is a miniature flexible thrombectomy catheter in the form of a rapid exchange fluid jet thrombectomy catheter having inflow orifices and outflow orifices located in wide pitch regions of the distal spiral metal tube.

Another significant aspect and feature of the present invention is the use of an all plastic guidewire exit port region which can be located anywhere from 2-38 cm from the tapered tip, but preferably about 17-25 cm from the tapered tip.

A further significant aspect and feature of the present invention is to provide a smaller miniature flexible thrombectomy catheter wherein a guidewire passes through only a portion of the device resulting in less pressure drop along the exhaust passage, and which can also improve the flow of dye through the catheter, thereby increasing catheter performance and procedural performances.

Having thus described various forms of the present invention and having mentioned some significant aspects and features of the present invention, it is the principal object of the present invention to provide a miniature flexible thrombectomy catheter and method of using same in order to remove thrombus or other unwanted material from a body blood vessel or other small regions of body cavities.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 8 illustrates the miniature flexible thrombectomy catheter connected to ancillary devices, and where FIG. 9 is a side view of the distal region of the miniature flexible thrombectomy catheter in the performance of the method of use thereof within a small blood vessel;

DETAILED DESCRIPTION OF THE PREFERRED EMBODIMENTS

Figure 1:
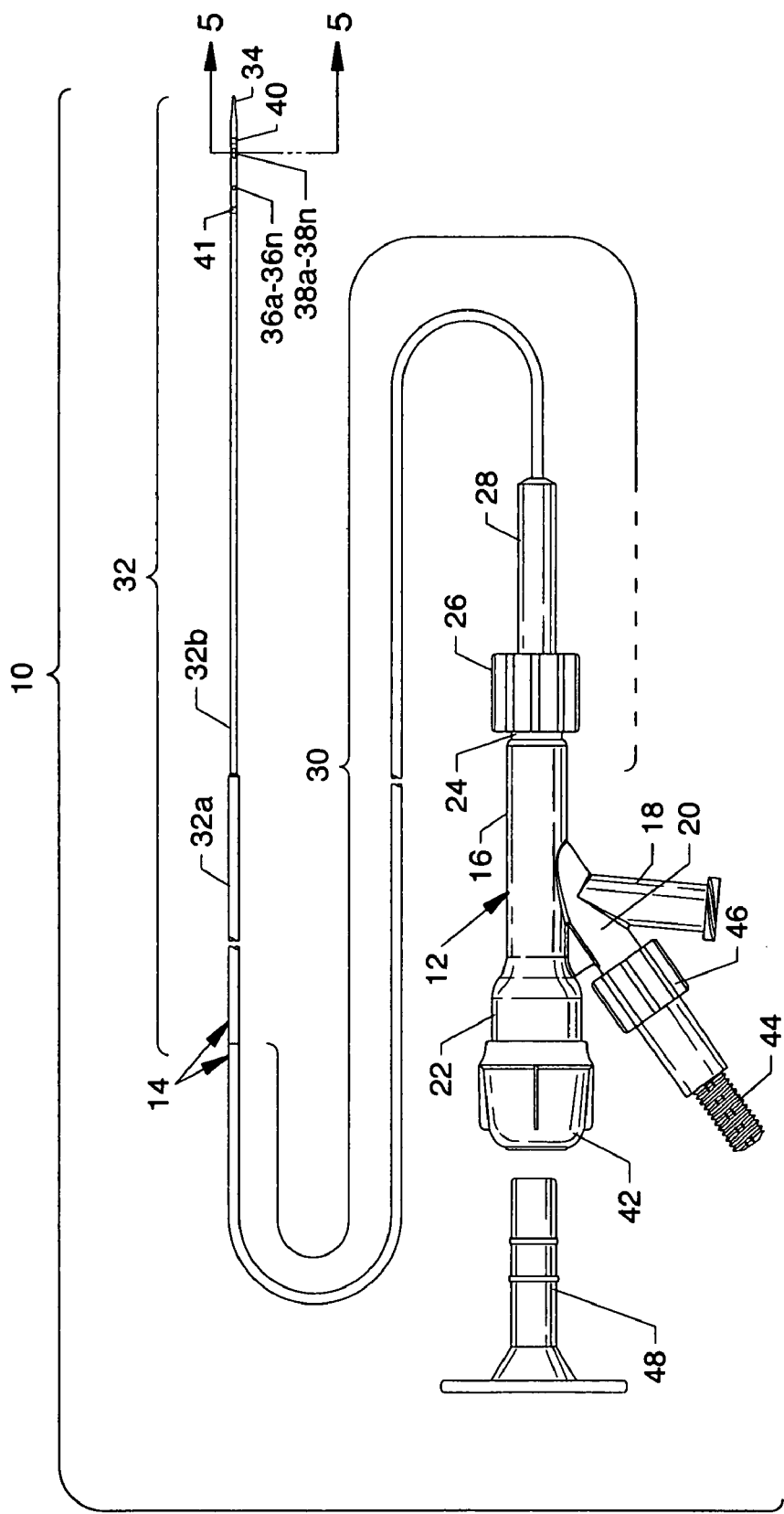
FIG. 1 is a plan view of the visible components of a miniature flexible thrombectomy catheter, the present invention.
Figure 6:
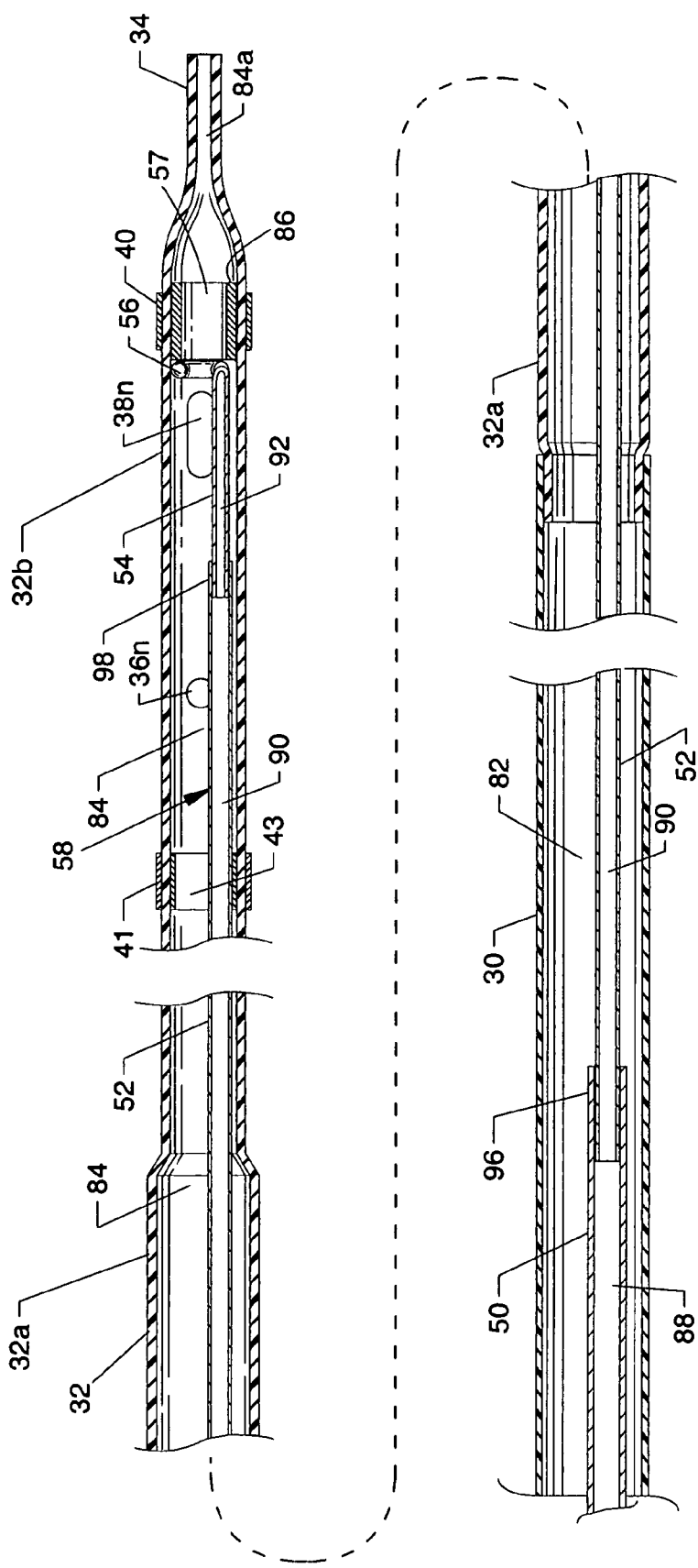
FIG. 6 shows the alignment of the jet body within the proximal tube and the distal tube.

FIG. 1 is a plan view of the visible components of a miniature flexible thrombectomy catheter 10, the present invention, including a one-piece manifold 12 having multiple structures extending therefrom or attached thereto and including a configured catheter tube 14 and other components as described herein. Preferably, the catheter tube 14 includes a hydrophilic coating to enhance deliverability along the vasculature or other structure. The visible portion of the one-piece manifold 12 includes a central tubular body 16, a threaded exhaust branch 18, and a high pressure connection branch 20 extending angularly from the central tubular body 16, a cavity body 22 extending proximally from the central tubular body 16 and partially shown and extending distally from the central tubular body 16, and a threaded connection port 24. The proximal end of the catheter tube 14 secures to the manifold 12 by the use of a Luer fitting 26 accommodated by the threaded connection port 24. The proximal end of the catheter tube 14 extends through a strain relief tube 28 and through the Luer fitting 26 to communicate with the manifold 12. The flexible catheter tube 14 is comprised of tubular components consisting of a flexible proximal tube 30 joined and connected to a shorter section of flexible distal tube 32 having multiple sections of different radii. The tubular components of the flexible catheter tube 14 are comprised of materials which promote pushability, torqueability, and which provide for operator feel. Preferably, the proximal tube 30 is comprised of braided polyimide, a synthetic polymeric resin or other suitable flexible material, and the distal tube 32 is comprised of Pebax, a thermoplastic elastomer, or other suitable flexible material. For purposes of illustration and example, the proximal tube 30 is 4 Fr as measured with reference to the French catheter scale. The distal tube 32 includes different radial sections, whereby a proximal section 32a of the distal tube 32 can be 4 Fr size to mate with the distal end of the proximal tube 30, and the distal section 32b of the distal tube 32 can be drawn and reduced or otherwise processed to 3 Fr size. The proximal end of the distal section 32a of the distal tube 32 is drawn down in size and inserted into and secured within the distal interior of the proximal tube 30 by adhesive or by any other suitable method, as shown in FIG. 6. The distal portion of the distal section 32b is tapered to form a flexible tip 34. Together, the proximal tube 30 and the distal tube 32 function as an exhaust tube for evacuation of macerated effluent from a thrombus or lesion site. The distal section 32b of the catheter tube 14 includes a plurality of outflow orifices 36a-36n and a plurality of inflow orifices 38a-38n, a proximally located radiopaque marker band 40 and a distally located radiopaque marker band 41. Also shown is a hemostasis nut 42 aligned to and threadingly engaged with the proximal region of the cavity body 22, and a threaded high pressure connection port 44 secured to the high pressure connection branch 20 by a Luer connector 46. An introducer 48 is also shown.

Figure 2:
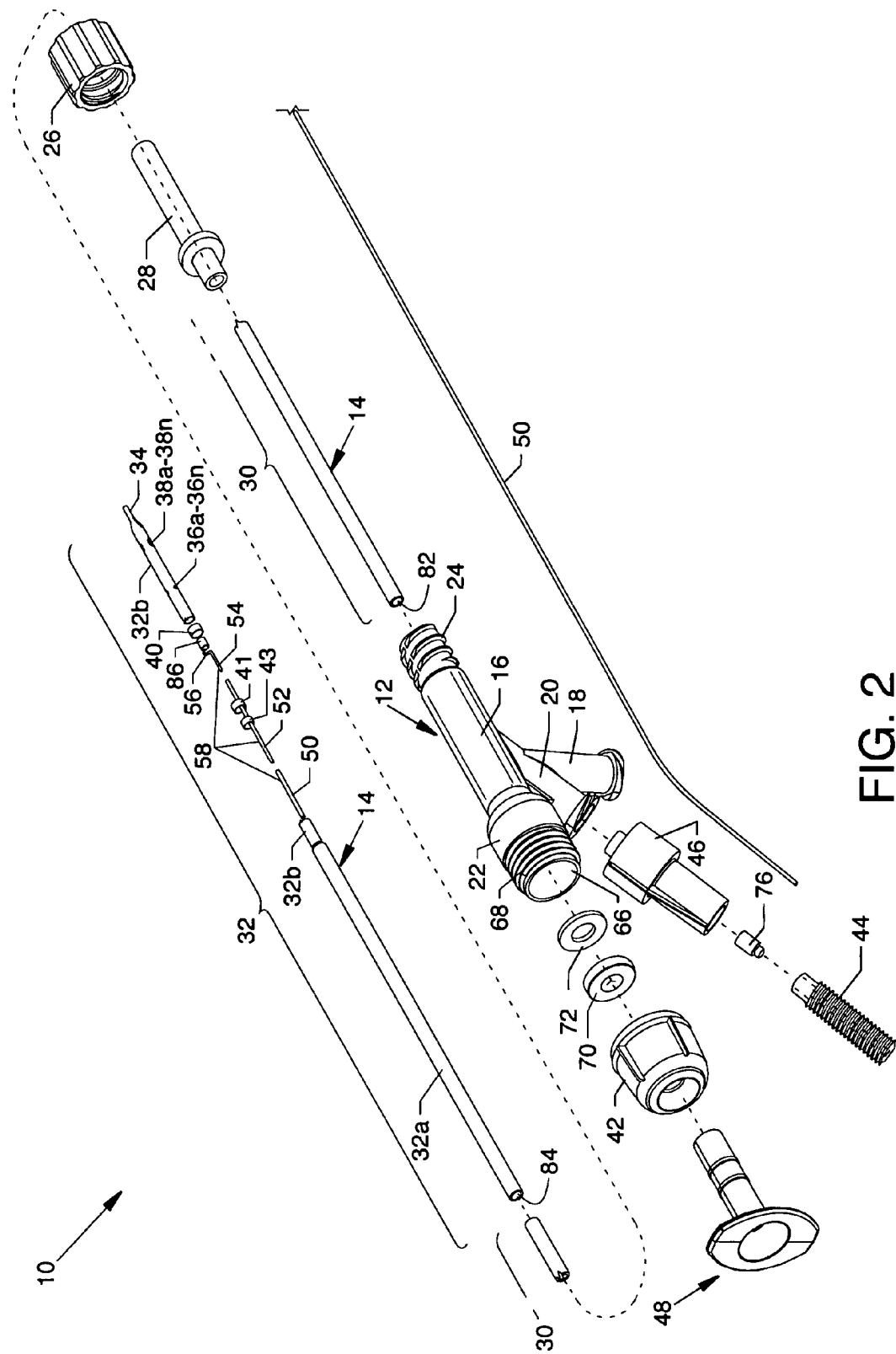
FIG. 2 is an isometric exploded and segmented view of the miniature flexible thrombectomy catheter.
Figure 3:
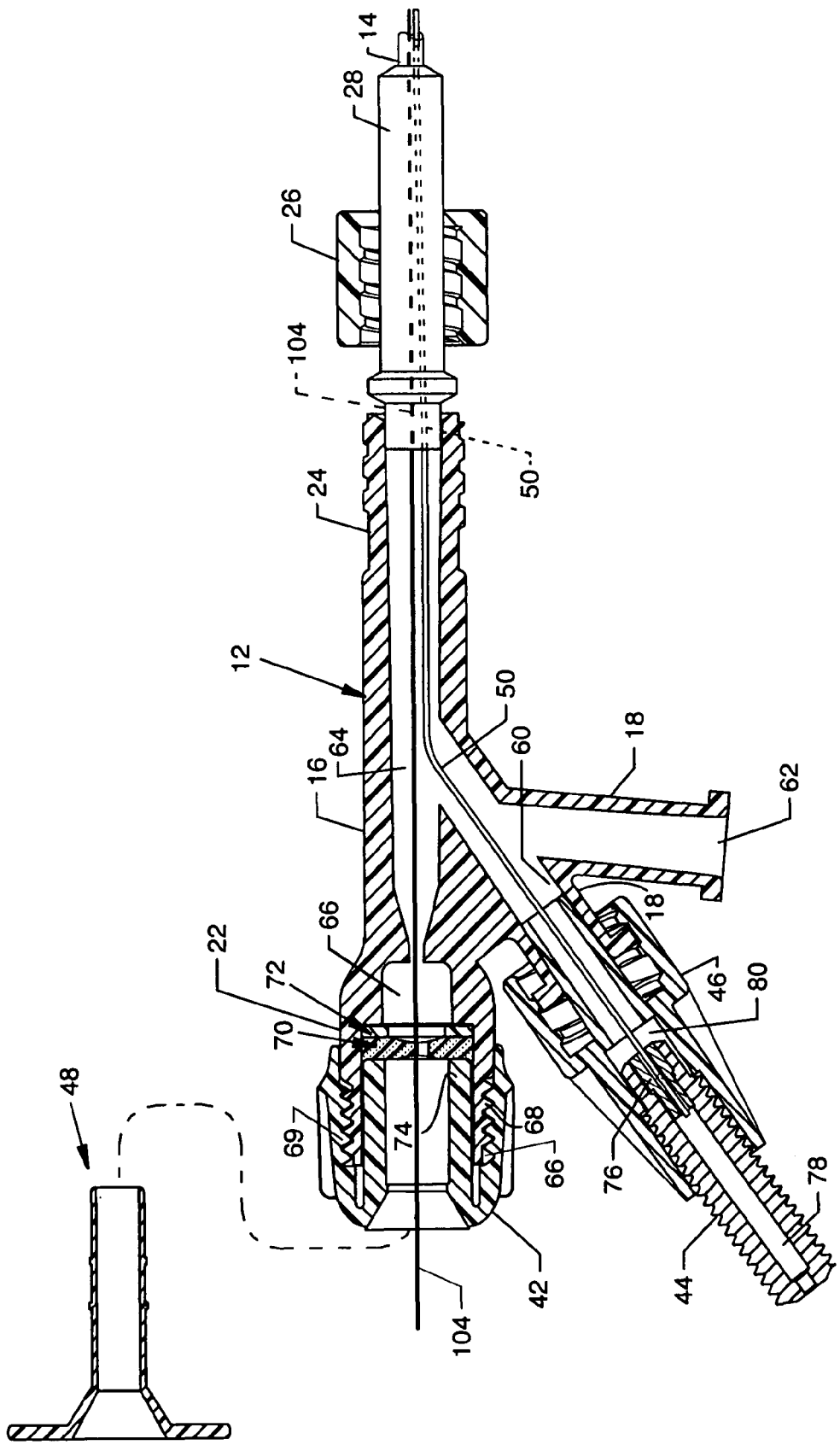
FIG. 3 is an assembled view in partial cross section of the components of the manifold and closely associated components and features thereof including a guidewire such as is incorporated in the use of the invention.

FIG. 2 is an isometric exploded and segmented view of the miniature flexible thrombectomy catheter 10, the present invention, and FIG. 3 is an assembled view in partial cross section of the components of the manifold 12 and closely associated components and features thereof, but including a guidewire 104, such as is incorporated in the use of the invention. As shown in FIGS. 1 and 2, the catheter tube 14 is comprised of the proximal tube 30 and the distal tube 32 which together serve and function as an exhaust tube.

A collection of assembled components, known as a jet body 58, delivers high pressure saline or other suitable fluid to the distal portion of the catheter tube 14 for creation of a cross stream jet. Such components are connected and include a proximally located flexible proximal high pressure tube 50, a flexible nitinol tube 52, and a relatively short flexible distal high pressure tube 54 having a fluid jet emanator 56 at the distal end. The proximal high pressure tube 50, preferably of stainless steel or other suitable material, passes through and is generally distal to the strain relief tube 28 and extends along a greater portion of and within the lumens of the catheter tube 14. The proximal end of the flexible nitinol tube 52 connects to the distal end of the proximal high pressure tube 50, whereby the flexible nitinol tube 52 extends distally from the distal end of the proximal high pressure tube 50. The proximal end of the distally located and relatively short flexible distal high pressure tube 54, preferably of stainless steel or other suitable material, is connected to the distal end of the nitinol tube 52 by a unique process, as later described in detail. The distal end of the distal high pressure tube 54, including the fluid jet emanator 56, is also shown in greater detail in FIGS. 4, 5, 6 and 7. A proximally located support ring 43, preferably of nitinol, is attached such as by a weldment to the nitinol tube 52 for support of the jet body 58 inside the proximal section 32b of the distal tube 32 in cooperation with the marker band 41. Some of the components forming the jet body 58 and other components are foreshortened and shown as partial lengths for the purpose of brevity and clarity.

With reference to FIGS. 2 and 3, the instant invention is further described. The manifold 12 includes connected and communicating passageways and cavities (FIG. 3) including a high pressure connection branch passageway 60, an exhaust branch passageway 62, a tapered central passageway 64 extending from and through the threaded connection port 24 and through the central tubular body 16 to and communicating with a multiple radius cavity 66, which preferably is cylindrical, located central to the cavity body 22. Threads 68 are located about the proximal portion of the cavity body 22 at the proximal region of the manifold 12 for accommodation of internal threads 69 to the hemostasis nut 42.

Beneficial to the instant invention is the use of a flexible self-sealing hemostasis valve 70 and a washer 72 which is located distal to the self-sealing hemostasis valve 70, the shapes of and the functions of which are described in the referenced copending patent application Ser. No. 10/455,096. The self-sealing hemostasis valve 70 and the washer 72 are aligned in and housed in the cavity 66 at the cavity body 22 at the proximal region of the manifold 12. The hemostasis nut 42 includes a centrally located cylindrical boss 74. The washer 72 and the self-sealing hemostasis valve 70 are captured in the greater radius portion of the cavity 66 by threaded engagement of the hemostasis nut 42 to the cavity body 20 of the manifold 12. The cylindrical boss 74 is brought to bear against the collective self-sealing hemostasis valve 70 and the washer 72 to resultingly bring pressure to bear as required against the self-sealing hemostasis valve 70 which pressure culminates in a forcible sealing of the self-sealing hemostasis valve 70 about a guidewire. Although one method of sealing against a guidewire is briefly shown and described it is appreciated that other methods can be incorporated into this and other forms of the instant invention such as in the referenced co-pending patent application Ser. No. 10/455,096.

Also shown is a ferrule 76 which is aligned within a passageway 78 of the threaded high pressure connection port 44 the combination of which is partially aligned within an interior passageway 80 of the Luer connector 46. The proximal end of the proximal high pressure tube 50, shown in segmented form in FIG. 2, is utilized for delivery of high pressure ablation liquids and is suitably secured in a center passage of the ferrule 76 to communicate with the interior passageway 78 of the threaded high pressure connection port 44, as shown in FIG. 3. The proximal high pressure tube 50 also extends through the high pressure connection branch passageway 60, through part of the tapered central passageway 64, through the strain relief tube 28 and Luer fitting 26, and through a lumen 82 of the proximal tube 30 where connection is made to the nitinol tube 52. As shown in FIG. 6, the nitinol tube 52 extends along the balance of the lumen 82 and thence through the lumen 84 of the proximal section 32a, thence through the continuing lumen 84 of the distal section 32b to connect to the shorter distal high pressure tube 54 within the proximal section 32b. It is noted that the lumen 84 having a variable diameter extends through the continuously fashioned proximal and distal sections 32a and 32b, respectively, comprising the distal tube 32. The shorter distal high pressure tube 54 continues to a support ring 86 where the fluid jet emanator 56 at the end of the shorter distal high pressure tube 54 is connected, such as by a weldment thereto, thereby supporting the shorter distal high pressure tube 54 and affixing the distal portion of the jet body 58 within the catheter tube 14.

Figure 4:
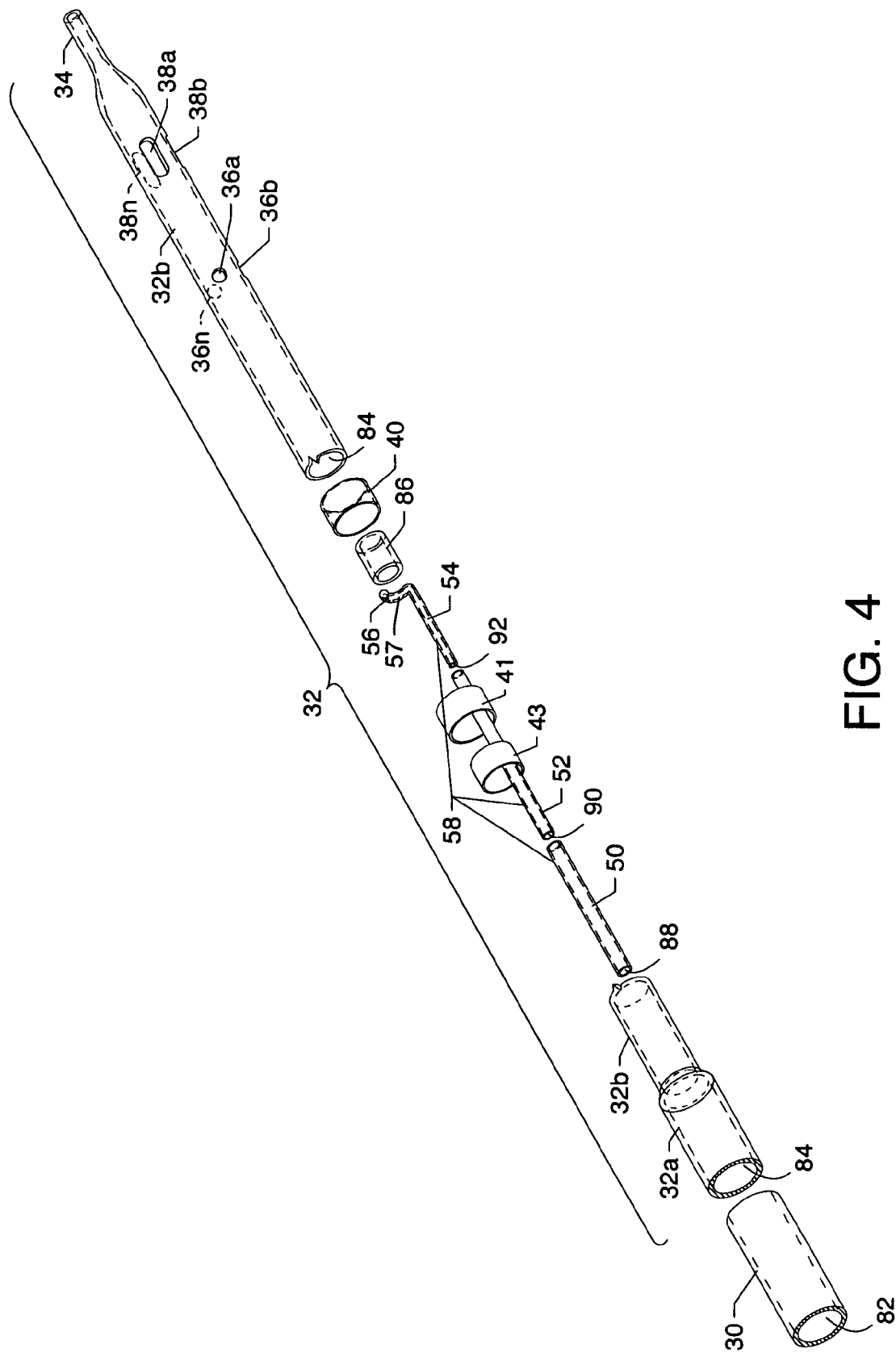
FIG. 4 is an exploded and sectioned isometric view of the distal tube of the invention including foreshortened portions of the proximal tube and of the components of a jet body which align and reside therein.
Figure 5:
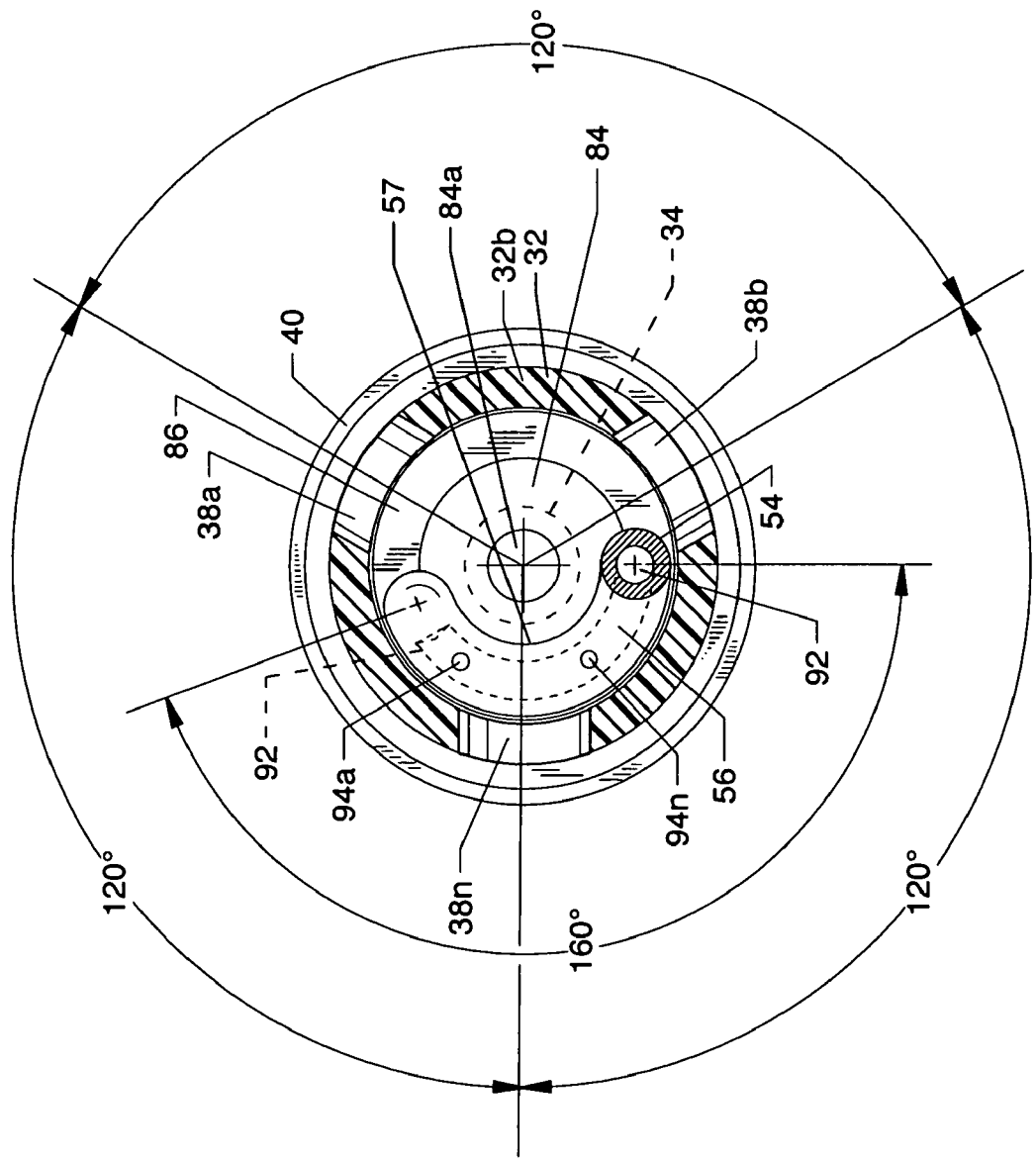
FIG. 5 is a cross section view along line 5-5 of FIG. 1 showing the spacing of the inflow orifices about the periphery of the proximal section of a distal tube.

FIG. 4 is an exploded and sectioned isometric view of the distal tube 32 including a short portion of the proximal tube 30 and of the components of the jet body 58 which are aligned therein. Especially shown are the connected lumens of the jet body 58, including a lumen 88 of the proximal high pressure tube 50, a lumen 90 of the nitinol tube 52, and a lumen 92 of the distal high pressure tube 54, whereby the lumen 92 extends within the fluid jet emanator 56 and is terminated within the end of the fluid jet emanator 56 (FIG. 5). The connected lumens transport high pressure saline or other fluids to the plurality of proximally directed jet orifices 94a-94n (FIG. 5) located in the proximal region of the fluid jet emanator 56 for the creation of a cross stream jet incorporating the outflow orifices 36a-36n and inflow orifices 38a-38n. To ensure structural integrity of the minimally sized distal section 32b, the outflow orifices 36a-36n, as well as the inflow orifices 38a-38n, are spaced at 120° intervals or other suitable intervals (FIG. 5) as opposed to 90° spacing intervals of larger prior art devices, thereby providing a sufficient quantity of material around and about the outflow orifices 36a-36n and inflow orifices 38a-38n to enhance robustness and to minimize buckling thereabout.

FIG. 5 is a cross section view along line 5-5 of FIG. 1 showing the spacing of the inflow orifices 38a-38n about the periphery of the distal section 32b of the distal tube 32. The outflow orifices 36a-36n are similarly spaced at 120°, as described in FIG. 4. Also shown is the portion of the lumen 92 and the connected jet orifices 94a-94n located along and about the fluid jet emanator 56. Current thrombectomy catheters include fluid jet emanators formed by bending hypotubing 90 degrees and then forming a 350+ degree loop. Such a loop configuration occupies excessive space in the catheter interior, therefore the present design incorporates the fluid jet emanator 56 in the form of an arcuate foreshortened loop which occupies less space. The arcuate fluid jet emanator 56 describes an arc of 160°, for the purpose of example and illustration, but may include an arc of other than 160°. The inwardly facing portion of the 160° arc of the fluid jet emanator 56 describes an arcuate passageway 57 also shown in FIG. 4. The 90 degree bend is formed near the distal portion of the distal high pressure tube 54 and is also bendingly directed in arcuate fashion slightly less than halfway around the circumference so that slightly less than one side of the distal section 32b of the distal tube 32 will include the distal fluid jet emanator 56 rather than the full circumference. Such a relationship allows passage of a guidewire in the space between the arcuate passageway 57 of the fluid jet emanator 56 and the opposed side of the distal section 32b, even though passage may not center along the central longitudinal axis of the distal section 32b of the distal tube 32. Even with the support ring 86 welded to the fluid jet emanator 56, the inner diameter is sufficient to pass the guidewire or even a guidewire lumen.

FIG. 6 shows the alignment of the jet body 58 within the proximal tube 30 and the distal tube 32. The attachment of the proximal high pressure tube 50 to the nitinol tube 52 is accomplished by using a proximal high pressure tube 50 which is slightly larger than the nitinol tube 52 to form an overlapping joint. The distal end of the proximal high pressure tube 50 is annealed. The proximal end of the nitinol tube 52 is inserted into the lumen 88 at the distal end of the proximal high pressure tube 50 and a sealed joint 96 is formed by rotary swaging the proximal high pressure tube 50 over, about and onto the proximal end of the nitinol tube 52 with a rotary swage device. Care in the selection of the size of the swaging dies requires attention for performing the swaging process to provide a circumferential leak-free seal of the stainless steel proximal high pressure tube 50 onto the nitinol tube 52 in order that over swaging will not result, thereby reducing the size of the lumen 90 of the nitinol tube 52 to cause an excessive flow restriction of the jet body 58.

Nitinol is not easily formed to be utilized in small radius applications and thus the distal high pressure tube 54 of stainless steel, which is more readily and more reliably formed with respect to nitinol, is incorporated into use, whereby the small radius arcuate fluid jet emanator 56 is fashioned at the distal end of the distal high pressure tube 54 in order to fit within the small radius lumen 84 of the distal section 32b. The proximal end of the distal high pressure tube 54 is mated within the distal end of the nitinol tube 52 to form a joint 98 by a new and unique laser swaging process, as described later in detail. It is noted that the lumen 84 of the distal section 32b continues through the distal section 32b and is reduced to a narrow section 84a at the flexible tip 34.

Prior art for joining tubular components has involved cryogenic processes, some of which are not entirely feasible nor practical. There have been cryogenic joints used where a nitinol tube is cooled whereby the nitinol assumes a plastic state suitable for being urged over the stainless steel tubing. As the nitinol tube warms, the nitinol tube wants to return to its former state, shrinks onto the stainless steel tube. Unfortunately, such a joint is challenging in the small dimensions of hypotubing. In general, the nitinol can only deform 6% to 8% before cracking. The inner diameter tolerance window for nitinol with an inner diameter of 0.008 inch exceeds 12%. Another joining method was developed called laser swaging. Direct laser welding of nitinol and stainless steel forms titanium ferrites, as described in the patents of Edison Welding Institute. These ferrites form cracks in the nitinol. Hence, a nickel filler for joining rod stock to rod stock was incorporated as a crack filler. By including enough filler, the titanium of the nitinol would not mix with the ferrous material in the stainless steel; however, the filler approach is difficult for tube joining. Edison Welding Institute uses a filler in a butt joint between a stainless steel rod and a nitinol rod.

In a novel approach to tube joining by laser swaging as accomplished in the present invention, the stainless steel distal high pressure tube 54 is plated with gold. The proximal end of the gold-plated stainless steel distal high pressure tube 54 is inserted into the lumen 90 at the distal end of the nitinol tube 52. The distal end of the nitinol tube 52 is welded down onto the proximal end of the gold-plated stainless steel distal high pressure tube 54 to form and seal joint 98. Power is adjusted so the materials meet, but do not mix, to accomplish a swage. The gold plating serves as a barrier for mixing and to inhibit penetration of the weld. The mechanism of this welding is that the nitinol tube 52 is actually being keyholed by the laser. Gold is highly reflective to the laser light used (1064 nm). Therefore, the laser light opens a hole in the nitinol and then reflects off the gold. The result is a nitinol tube 52 which is essentially swaged onto a gold-plated stainless steel distal high pressure tube 54 with a laser. The gold-plated stainless steel distal high pressure tube 54 is then annealed in the region that will be bent and formed to form the fluid jet emanator 56. The annealing enables the distal portion of the stainless steel distal high pressure tube 54 to be readily formed into a distally located semicircle (half loop), i.e, the fluid jet emanator 56. The annealing also removes the thin layer of gold from the surface of the exposed distal stainless steel tube 54. The stainless steel fluid jet emanator 56 can be electrical discharge machined or otherwise processed to form the proximally directed jet orifices 94a-94n in the loop portion of the fluid jet emanator 56.

Figure 7:
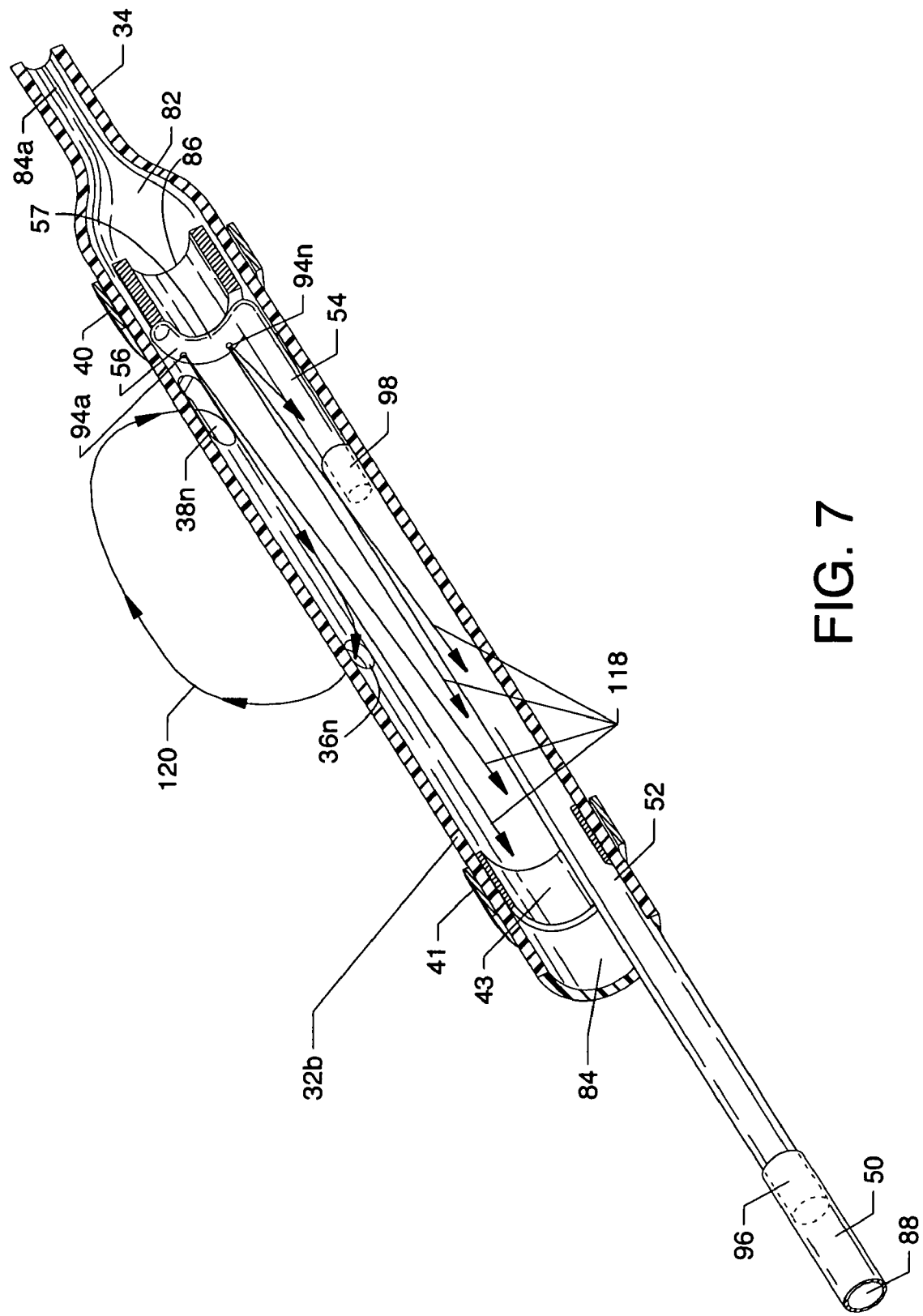
FIG. 7 is an isometric cutaway view of the distal portion of the proximal section at one end of the distal tube showing high velocity fluid jet stream directed rearwardly from the jet orifices of the fluid jet emanator to form one or more cross stream jets.

FIG. 7 is an isometric cutaway view of the distal portion of the proximal section 32b at one end of the distal tube 32 showing high velocity fluid jet stream 118 directed rearwardly from the jet orifices 94a-94n of the fluid jet emanator 56 to form one or more cross stream jets 120. The operation of the cross stream jets 120 is further described in FIG. 9.

Mode of Operation

Figure 8:
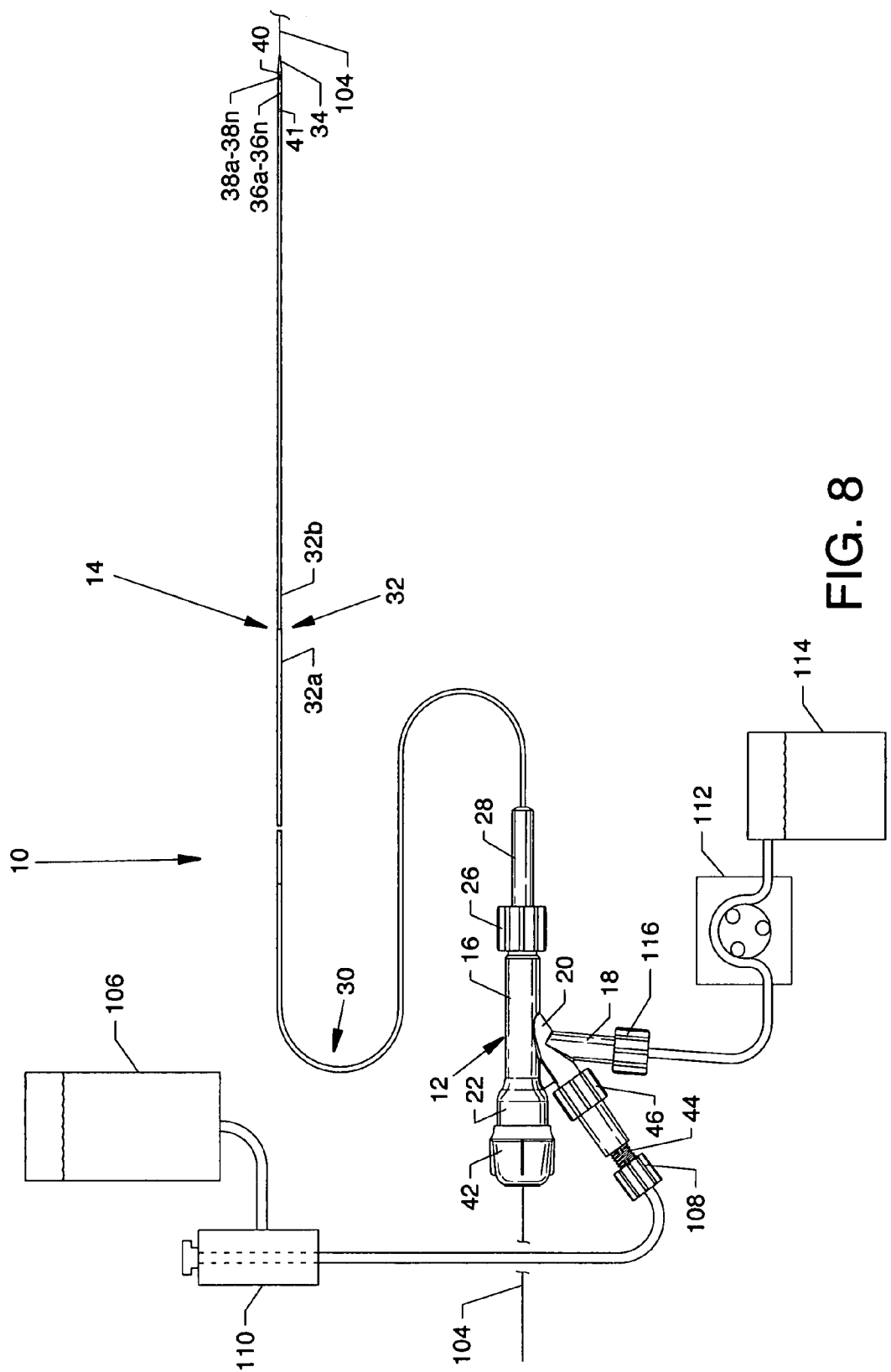
FIGS. 8 and 9 illustrate the mode of operation of one form of the present invention, where
Figure 9:
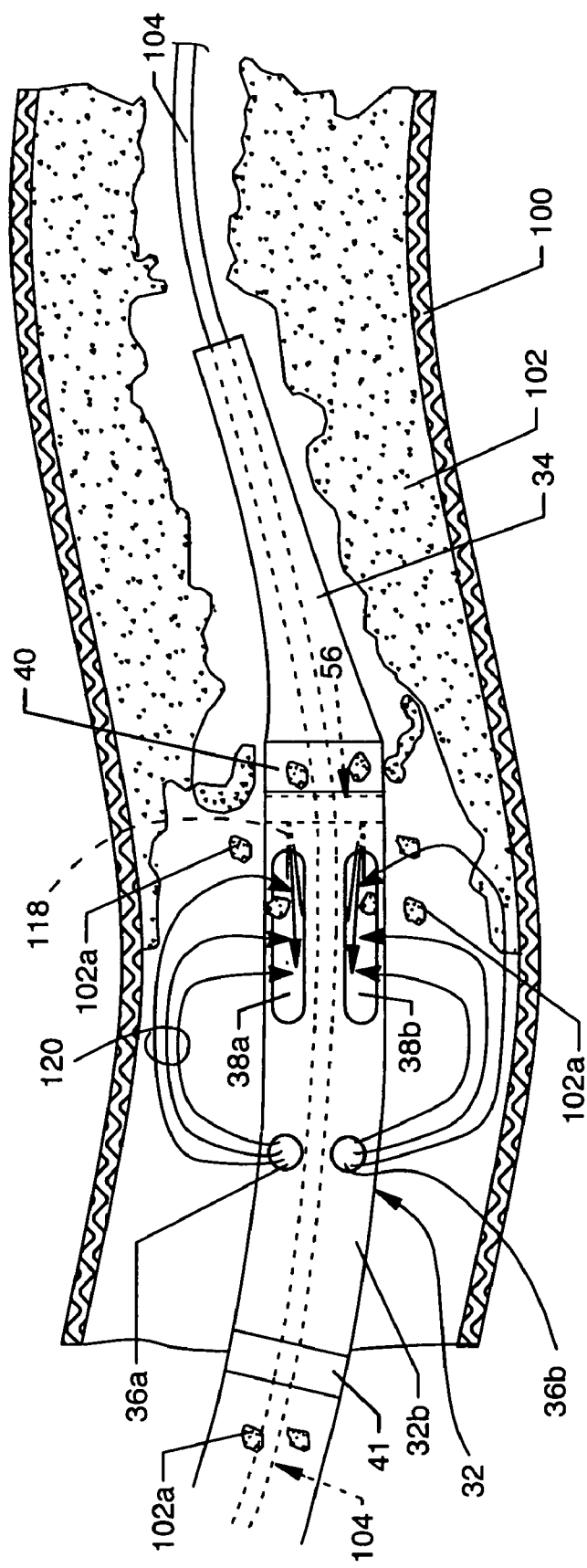

FIGS. 8 and 9 illustrate the mode of operation of one form of the present invention, where FIG. 8 illustrates the miniature flexible thrombectomy catheter 10 connected to ancillary devices, and where FIG. 9 illustrates a side view of the distal region of the miniature flexible thrombectomy catheter 10 in the performance of the method of use thereof within a small blood vessel 100 (shown in cross section) at a site of a thrombotic deposit or lesion 102. The mode of operation is best understood by referring to FIGS. 8 and 9, as well as previously described figures.

In FIG. 8, the miniature flexible thrombectomy catheter 10 is shown engaged over and about a guidewire 104 where the guidewire 104 engages the lumen 84 of the distal tube 32 at the tapered tip 34 of the distal tube 32 followed by passage through the lumen 82 of the proximal tube 30, thence sealingly through the manifold 12 and closely associated components thereof to exit therefrom through the hemostasis nut 42. A high pressure fluid source 106 and a high pressure fluid pump 110 connect, as shown, to the manifold 12 via the threaded high pressure connection port 44 by Luer connector 108 or optionally by a direct connection to supply high pressure saline or other suitable fluid for the miniature flexible thrombectomy catheter 10. An optional exhaust regulator 112 and a collection chamber 114 connect to the threaded end of the threaded exhaust branch 18 of the manifold 12 by a Luer fitting 116, as shown, for influencing the outflow from the miniature flexible thrombectomy catheter 10.

FIG. 9 is a side view of the miniature flexible thrombectomy catheter 10 in the performance of the method of use thereof, with particular attention given to the distal section 32b of the distal tube 32 including the flexible tapered tip 34 positioned in a blood vessel 100 at a site of a thrombotic deposit or lesion 102. Multiple high velocity fluid jet streams 118 of saline, for example, or other suitable fluid, are shown being emitted in a proximal direction from the fluid jet emanator 56 to impinge upon thrombotic deposits or lesions 102 to carry and urge particulate thereof proximally. Other fluid jet emanators of appropriate size and/or configuration can be incorporated within the distal section 32b of the distal tube 32 as an alternative to the fluid jet emanator 56 to emanate or emit one or more high velocity fluid jet streams 118 distally along or near the longitudinal axis of the distal tube 32 to accomplish the same purpose as that described for the fluid jet emanator 56. The high velocity fluid jet streams 118 of saline pass outwardly through the outflow orifices 36a-36n creating cross stream jets 120 (lower velocity jets) directed outwardly toward the wall of the blood vessel 100 and are influenced by the low pressure at the inflow orifices 38a-38n to cause the cross stream jets 120 to flow circumferentially and distally to impinge on, provide drag forces on, and break up thrombotic deposits or lesions 102, and to, by entrainment, urge and carry along one or more particles 102a of thrombotic deposits or lesions 102 through the inflow orifices 38a-38n, a relatively low pressure region, into the high velocity fluid jet streams 118 where the thrombus is further macerated into microscopic particles, and then into the distal tube lumen 84 (FIG. 4). A certain portion of this macerated debris which is mixed with fresh saline is removed through the distal tube lumen 84 and a certain portion flows back out the outflow orifices 36a-36n and recirculates to break up more debris which is returned to the inflow orifices 38a-38n. In this way, much more fluid flow circulates through the system than is injected through the jet orifices 94a-94n. For purposes of illustration and example, three to ten times more flow circulates through the system than is delivered by the jet orifices 94a-94n. The entrainment through the inflow orifices 38a-38n is based on entrainment by the high velocity fluid jet streams 118. The outflow is driven by internal pressure which is created by the high velocity fluid jet streams 118 and the fluid entrained through the inflow orifices 38a-38n. Enhanced clot removal is attainable because of the recirculation pattern established between outflow and inflow orifices 36a-36n and 38a-38n, which creates a flow field that maximizes drag force on the wall-adhered thrombus. Since the entrained thrombus is macerated into microscopic particles, those particles that exit the outflow orifices 36a-36n are not of sufficient size to significantly block the distal circulation, and will be re-entrained into the inflow orifices 38a-38n at a high rate. In a no-flow situation or when flow is stopped with another device such as an occlusive balloon, material can then be recirculated and rediluted until all that remains is saline and all particles are removed.

Figure 10:
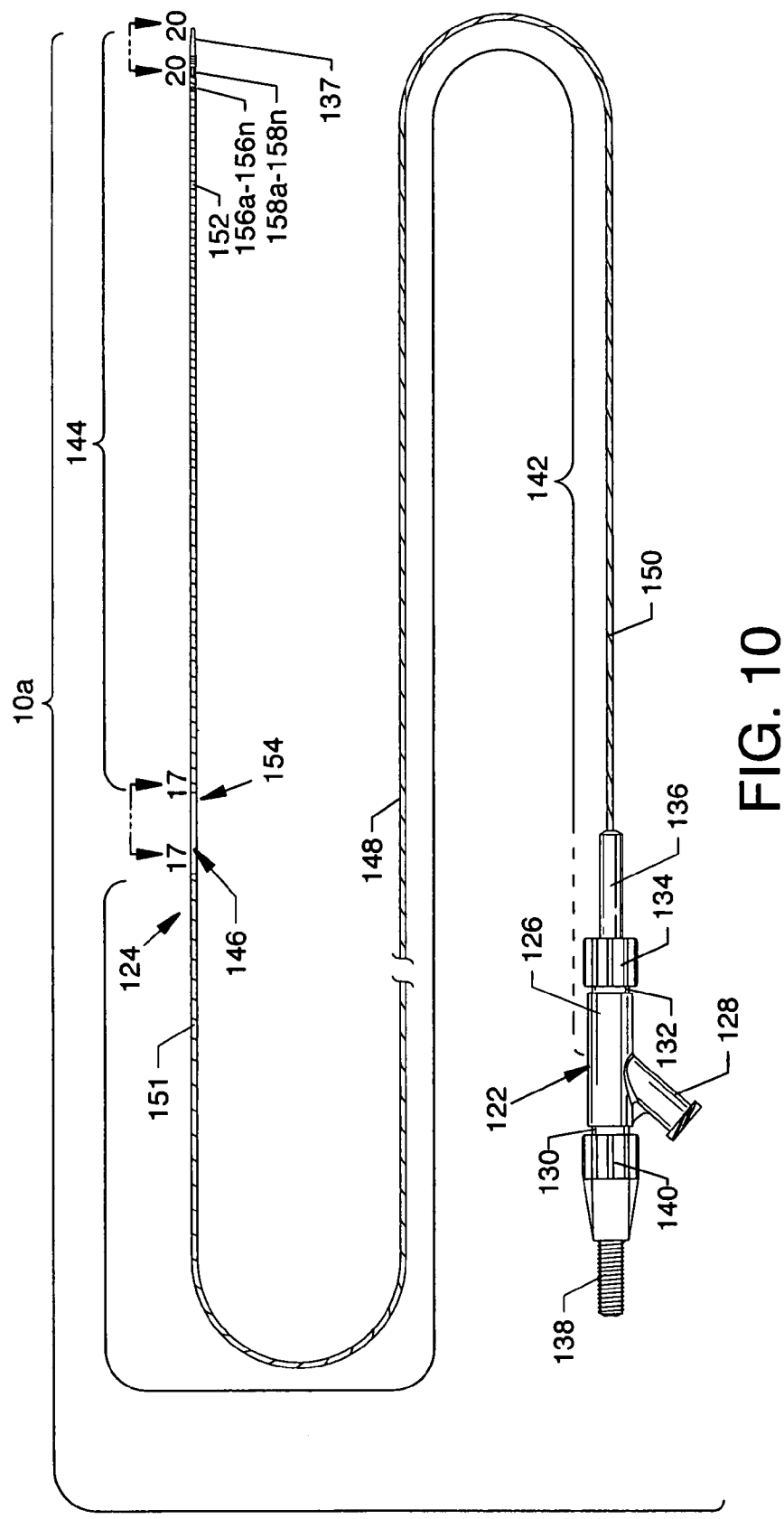
FIG. 10 is a plan view of the visible components of another form of the miniature flexible thrombectomy catheter.

FIG. 10 is a plan view of the visible components of another form of the miniature flexible thrombectomy catheter 10, herein designated as the miniature flexible thrombectomy catheter 10a, the present invention, employing many components and teachings of the first form of the present invention. The distal portion of the miniature flexible thrombectomy catheter 10a includes a one-piece manifold 122 having multiple structures extending therefrom or attached thereto including a configured catheter tube 124 distal to the manifold 122, as well as other components attached to the structure of the manifold 122 as described herein. Preferably, the catheter tube 124 includes a hydrophilic coating and a thin and flexible plastic polymer jacket covering to enhance deliverability along the vasculature. The visible portion of the one-piece manifold 122 includes a central tubular body 126, a threaded exhaust branch 128 extending angularly from the central tubular body 126, a threaded connection port 130 extending proximally from the central tubular body 126, and a threaded connection port 132 partially shown extending distally from the central tubular body 126. The proximal end of the catheter tube 124 is secured to the manifold 122 by the use of a Luer fitting 134 accommodated by the threaded connection port 132. The proximal end of the catheter tube 124 extends through a strain relief tube 136 and through the Luer fitting 134 to communicate with the manifold 122. A threaded high pressure connection port 138 threadingly engages a Luer fitting 140, whereby the Luer fitting 140 connectingly engages the threaded connection port 130.

The catheter tube 124 comprises a substantially unitary, continuous, elongated, tubular structure containing or hosting various components and serving as an exhaust path extending distally from inside the manifold 122 and through the strain relief tube 136 and terminating at or near a flexible tapered tip 137 fashioned of suitable flexible silicone or other flexible rubber like material. The catheter tube 124, which is substantially continuous except for a short portion, consists of connected tubular components including a proximal spiral metal tube 142 and a distal spiral metal tube 144 preferably of a smaller cross section dimension of the proximal spiral metal tube 142, connected by a short configured intermediate tube 146, preferably of Pebax or other suitable flexible material, therebetween. The proximal spiral metal tube 142 and the distal spiral metal tube 144 can be laser cut or otherwise suitably fashioned. The pitch of the cut can be progressively or otherwise varied along the length of the proximal spiral metal tube 142 and the distal spiral metal tube 144 comprising the majority of the catheter tube 124. The use of the proximal spiral metal tube 142, the distal spiral metal tube 144, and the interceding intermediate tube 146 instead of the easily kinkable, stiff, projecting metal tube of previous designs, preserves the excellent pushability and torqueability of previous designs, but is less kinkable and more flexible than previous designs. The spiral cut along the length of the catheter tube 124, i.e., the proximal spiral metal tube 142 and the distal spiral metal tube 144, can be progressively transitioned or otherwise varied in pitch from distal to proximal to produce a continuous transition from flexible to stiff which maximizes the pushability and "feel" of the catheter tube 124. Although the pitch of the spiral cuts are shown as uniformly progressive, the spiral cut along the proximal spiral metal tube 142 and the distal spiral metal tube 144 can be of various pitch configurations to achieve the desired property. During manufacturing, the length of the proximal spiral metal tube 142 and the distal spiral metal tube 144 can be extended or shortened anywhere along the length of the catheter tube 124, or the pitch can be configured to provide a desired mechanical property. A polymer jacket 148, which can be transparent and which can be in the form of a shrink tube or other suitable configuration or material, encompasses the catheter tube 124, thus creating a leak-free tubular structure, as well as adding mechanical and lubricious properties to the catheter tube 124. In the alternative, a polymer tube, such as, but not limited to, Pebax can be drawn down to encompass the catheter tube 124. For example and for purposes of illustration, a uniformly progressive pitch of the proximal spiral metal tube 142 and the distal spiral metal tube 144 can be seen through the preferably clear polymer jacket 148 if a transparent polymer is incorporated, starting with a wide pitch shown at 150 of the proximal spiral metal tube 142 at or near the strain relief tube 136 transitioning to a close pitch shown at 152 at or near the distal end of the distal spiral metal tube 144. A guidewire tube exit region 154 is located along the intermediate tube 146 and the proximal portion of a guidewire tube 155 having a lumen 157 (FIG. 15) is located at the guidewire tube exit region 154, as later described in detail. A plurality of outflow orifices 156a-156n and a plurality of inflow orifices 158a-158n corresponding to and having an operational function similar to that of the plurality of outflow orifices 36a-36n and the plurality of inflow orifices 38a-38n of the miniature flexible thrombectomy catheter 10, are located about the distal region of the catheter tube 124, and more specifically, at a location about the distal spiral metal tube 144 near the flexible tapered tip 137.

For purposes of demonstration and example, the proximal spiral metal tube 142 is slightly larger than 3 Fr, as measured with reference to French catheter scale. Correspondingly, the distal spiral metal tube 144 can also be slightly larger or smaller than 3 Fr. The intermediate tube 146 can be of an appropriate size and configuration to mate with the distal end of the proximal spiral metal tube 142 and the proximal end of the distal spiral metal tube 144. Together, the proximal spiral metal tube 142 and the distal proximal spiral metal tube 144 in combination with the intermediate tube 148 function as an exhaust tube for evacuation of macerated effluence from a thrombus or lesion site. It is appreciated that the cross section dimension of the distal spiral metal tube 144 preferably is somewhat less than the cross section dimension of the proximal spiral metal tube 142, thereby providing a greater degree of flexibility to the distal portion of the catheter tube 124, such as taught with respect to the catheter tube 14 of the miniature flexible thrombectomy catheter 10.

Figure 11:
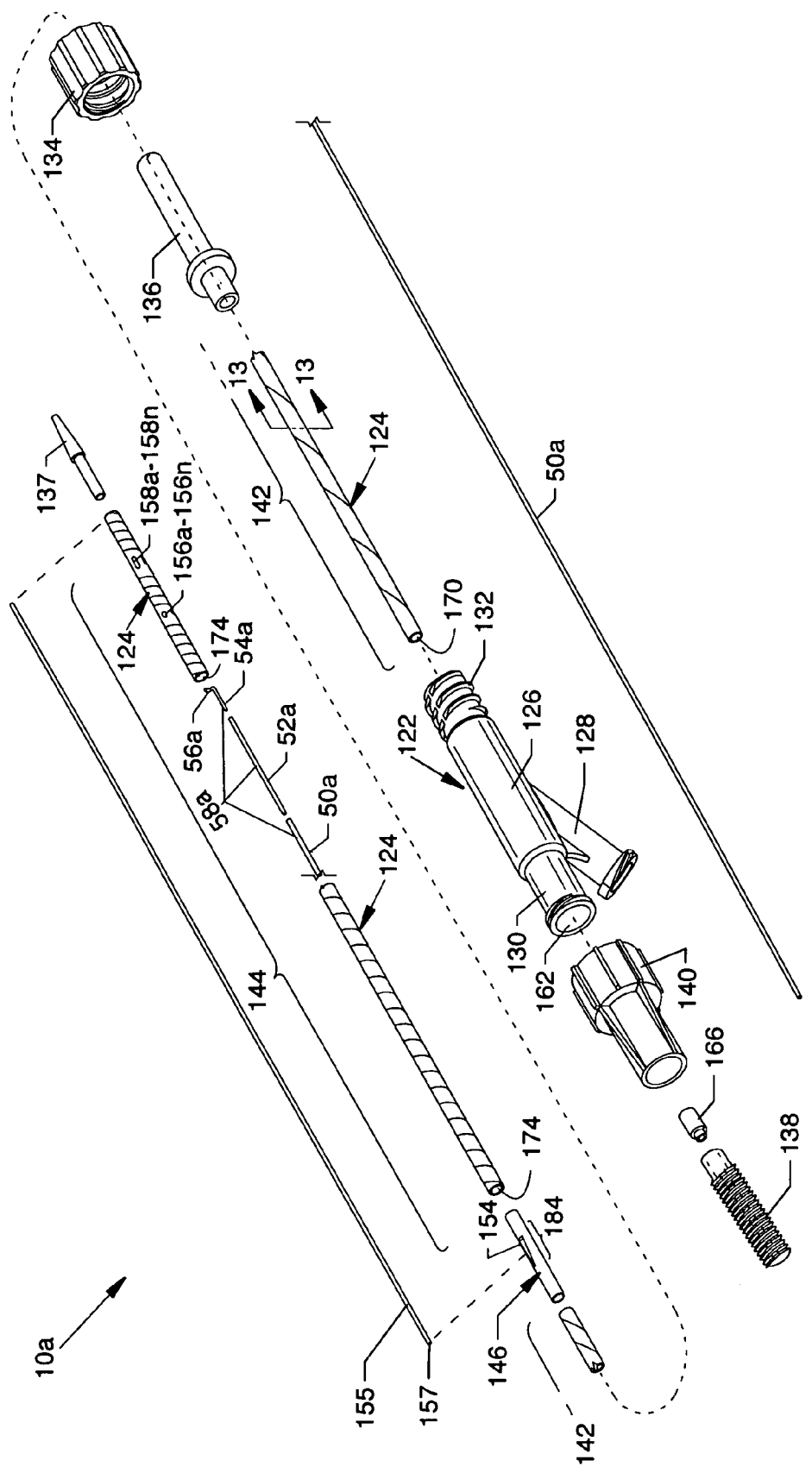
FIG. 11 is an isometric exploded and segmented view of the miniature flexible thrombectomy catheter of FIG. 10.
Figure 12:
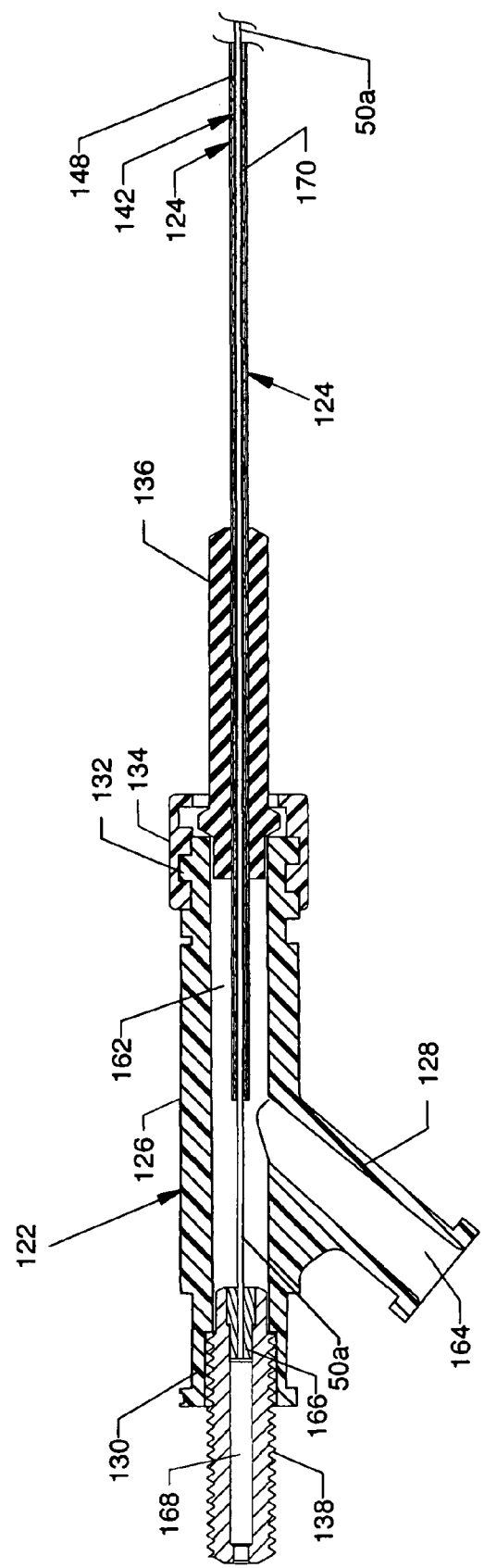
FIG. 12 is an assembled view in cross section of the components of the manifold of FIG. 11 and closely associated components and features thereof, as well as showing the inclusion of and the accommodation of the catheter tube.

FIG. 11 is an isometric exploded and segmented view of the miniature flexible thrombectomy catheter 10a, the present invention, and FIG. 12 is an assembled view in cross section of the components of the manifold 122 and closely associated components and features thereof, as well as showing the inclusion of and the accommodation of the catheter tube 124. As shown in FIG. 10, the catheter tube 124 is comprised of the proximal spiral metal tube 142 and the distal spiral metal tube 144 and the intermediate tube 146 which, together and collectively, serve and function as an exhaust tube.

Figure 15:
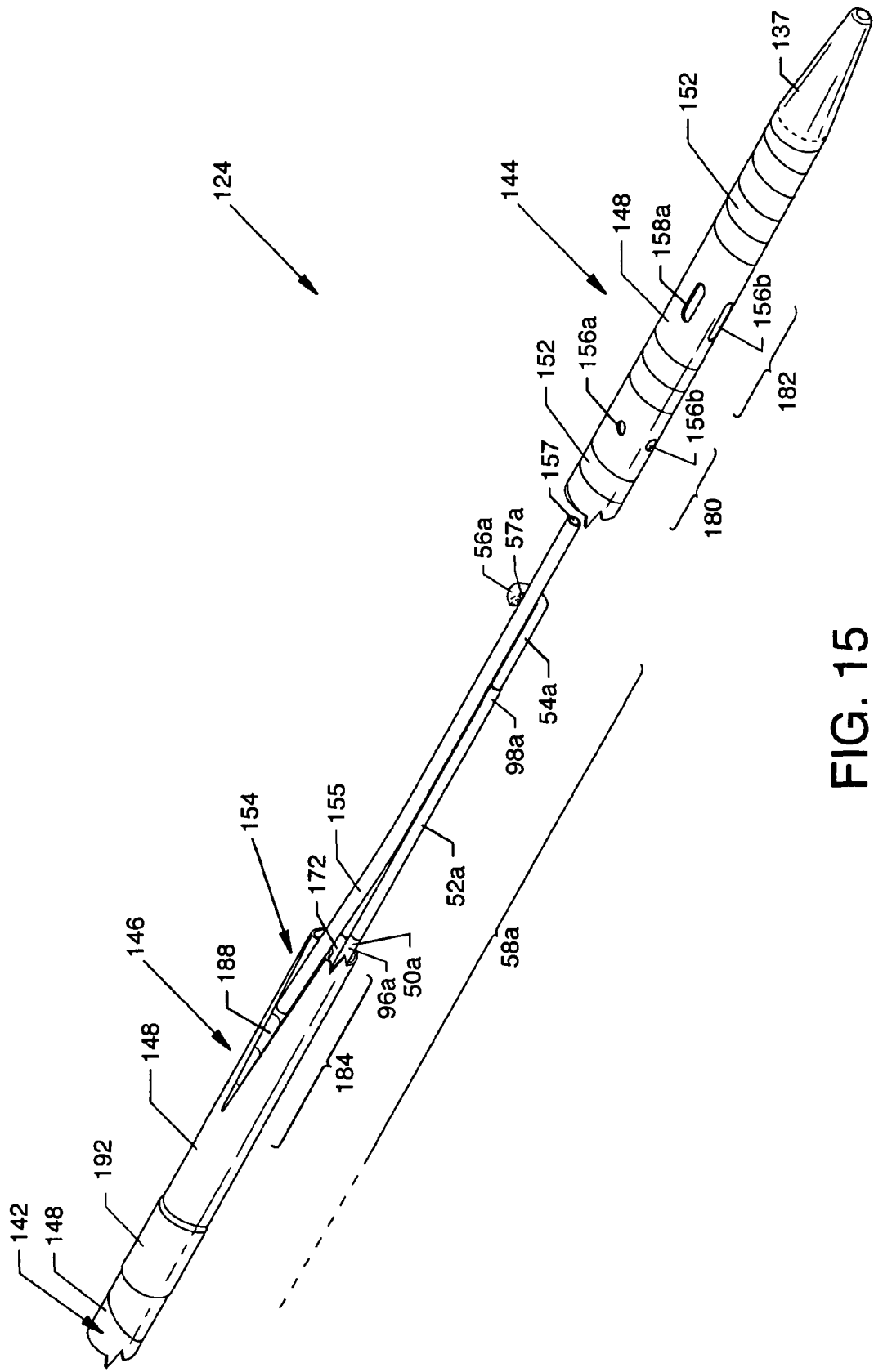
FIG. 15 is a foreshortened exploded and separated isometric view of the components of the catheter tube extending from and including the proximal spiral metal tube to the tapered tip.

A jet body 58a similar in most respects in construction and in the method of construction to the jet body 58 of the miniature flexible thrombectomy catheter 10 delivers high pressure saline or other suitable fluid to the distal portion of the catheter tube 124 for creation of cross stream jets. Such similar components comprising the jet body 58a are suffixed by the letter "a" and are connected and include the proximally located flexible proximal high pressure tube 50a, which in this form includes a straight proximal end, the flexible nitinol tube 52a, and the distally located relatively short flexible distal high pressure tube 54a having the fluid jet emanator 56a at the distal end. Joints 96a and 98a are shown in FIG. 15. The proximal high pressure tube 50a, preferably of stainless steel or other suitable material, passes through and is generally distal to the strain relief tube 136 and extends along a greater portion of and within the lumens of the catheter tube 124. Some of the components forming the jet body 58a and other components are foreshortened and shown as partial lengths for the purpose of brevity and clarity.

With reference to FIG. 12, the instant invention is further described. The manifold 122 includes connected and communicating passageways including a central passageway 162 extending from and through the threaded connection port 132 and thence through the central tubular body 126 to and communicating with and connecting to and being a part of the interior of the threaded connection port 130. An exhaust branch passageway 164 central to the threaded exhaust branch 128 communicates with the central passageway 162.

Also shown is a ferrule 166 which aligns within a passageway 168 of the threaded high pressure connection port 138, the combination of which is partially accommodated within the proximal portion of the central passageway 162 of the manifold 122. The proximal end of the proximal high pressure tube 50a is utilized for delivery of high pressure ablation liquids and suitably secures in a center passage of the ferrule 166. The proximal high pressure tube 50a also extends directly through the central passageway 162, through the lumen 170 (FIG. 13) of the proximal spiral metal tube 142, through a lumen 172 (FIG. 16) of the intermediate tube 146, and partially through and along proximal portion of the lumen 174 of the distal spiral metal tube 144 at or near where connection is made to the nitinol tube 52a.

Figure 13:
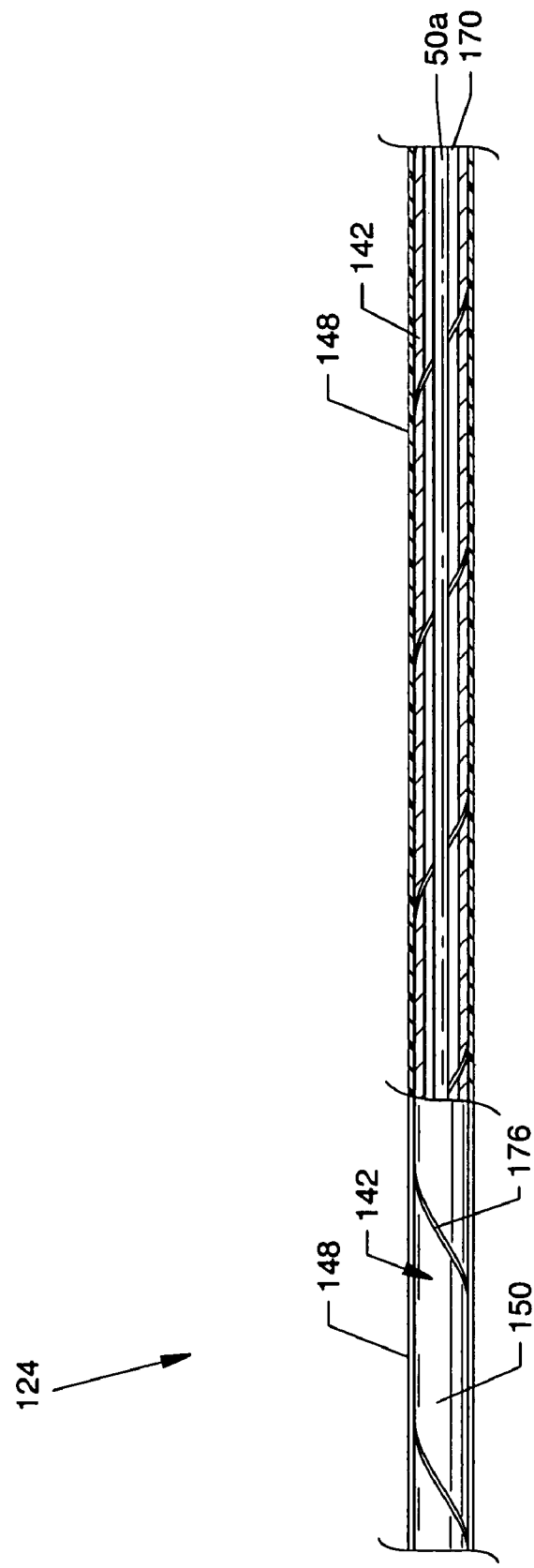
FIG. 13 is a partial cross section view of the catheter tube along line 13-13 of FIG. 11.
Figure 14:
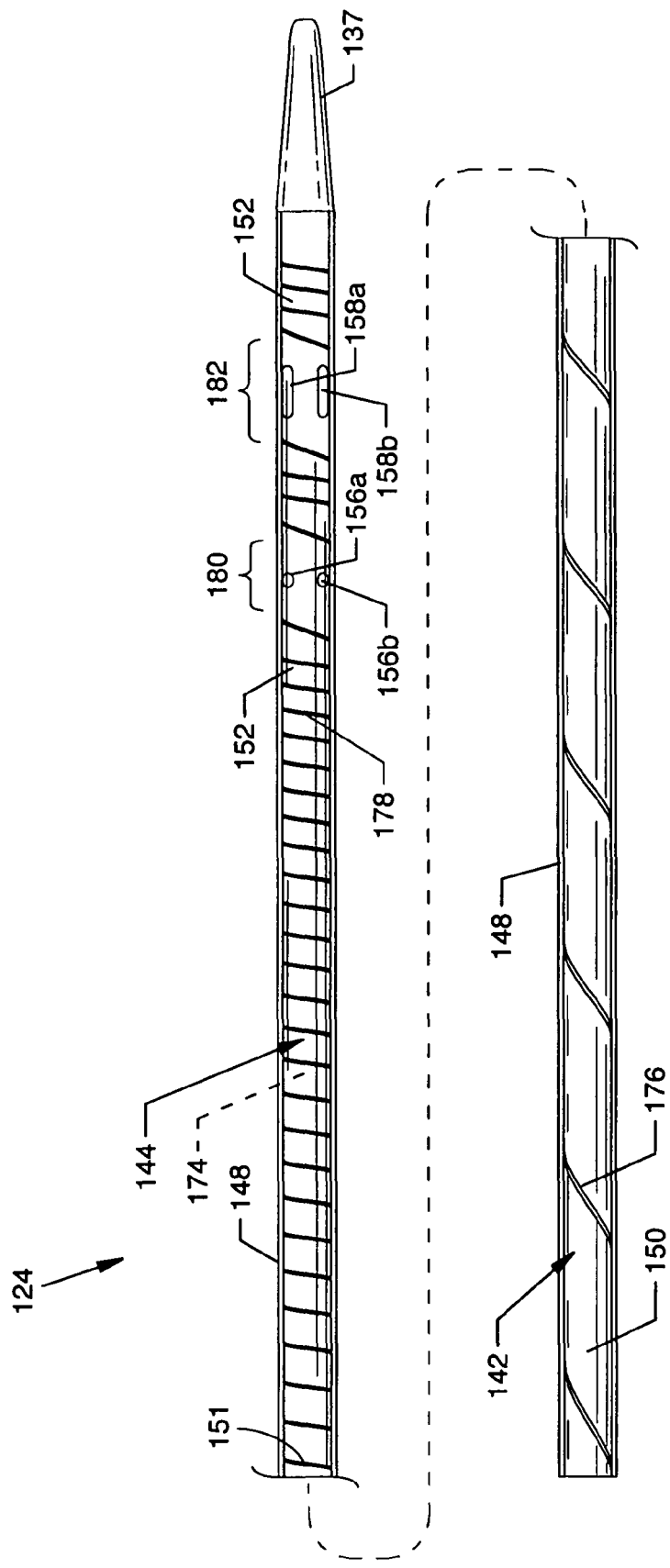
FIG. 14 is a divided side view of the catheter tube showing extremes of the proximal spiral metal tube and the distal spiral metal tube.

FIG. 13 is a partial cross section view of the catheter tube 124 along line 13-13 of FIG. 11, and FIG. 14 is a divided side view of the catheter tube 124 showing extremes of the proximal spiral metal tube 142 and the distal spiral metal tube 144. Provided that the material of the polymer jacket 148 encasing the proximal spiral metal tube 142 and the distal spiral metal tube 144 is transparent, the proximal spiral metal tube 142 and the distal spiral metal tube 144 are easily viewed therethrough. A proximal spiral cut 176 extends along and about the proximal spiral metal tube 142 and a distal spiral cut 178 extends along and about the distal spiral metal tube 144, whereby the substantially full length polymer jacket 148 is closely aligned over and about the proximal spiral cut 176 of the proximal spiral metal tube 142 and closely aligned over and about the distal spiral cut 178 of the distal spiral metal tube 144, as well as over and about the exterior of the intermediate tube 146 (FIG. 11) which also is visible. The proximal spiral cut 176 and the distal spiral cut 178 can be produced by a laser cutting tool, or other suitable fashioning methods can be incorporated into use in the substantially continuous catheter tube 124 which can include various spiral pitch configurations. One configuration, as also shown in FIG. 10, in which, for purposes of example and illustration, there are adjacent continuous sections of the proximal spiral metal tube 142 formed by the proximal spiral cut 176 having a wide pitch 150 which can be a constant pitch or changing progressive pitch transitioning to a medium pitch 151 as formed by the proximal spiral cut 176 which can be a constant pitch or changing progressive pitch, and lastly there are adjacent continuous sections of the distal spiral metal tube 144 formed by the distal spiral cut 178 having a close pitch 152 which can be a constant pitch or changing progressive pitch.

Additional wide pitch regions 180 and 182 interrupting the close pitch 152 of the distal spiral metal tube 144 for accommodation of the outflow orifices 156a-156n and the inflow orifices 158a-158n are shown in FIG. 14. Many configurations can be incorporated to achieve required pushability and torqueability to meet different criteria, whereby the wide pitch, the medium pitch, and the close pitch features can populate various locations along the proximal spiral metal tube 142 and/or the distal spiral metal tube 144.

FIG. 15 is an exploded and separated isometric view of the components of the catheter tube 124 extending from and including the proximal spiral metal tube 142 to the tapered tip 137, some components being foreshortened with respect to length for the purpose of illustration and clarity. The shown portion of the catheter tube 124 includes the spiral metal tube 142, the polymer jacket 148, the intermediate tube 146 including the formed portion 184, the flexible guidewire tube 155 of polymer construction, the proximal high pressure tube 50a, the nitinol tube 52a, the distal high pressure tube 54a, the fluid jet emanator 56a, the distal spiral metal tube 144, and other components and features within, along and about the catheter tube 124.

The proximal high pressure tube 50a with a lumen 88a (FIGS. 18 and 19) extends from the manifold 122, as previously described, through the lumen 170 in the proximal spiral metal tube 142, through the lumen 172 of the intermediate tube 146 at or near which point the proximal high pressure tube 50a connects to the proximal end of the nitinol tube 52a. The distal end of the nitinol tube 52a is connected to the proximal end of the distal high pressure tube 54a having the included fluid jet emanator 56a, whereby the nitinol tube 52a and the distal high pressure tube 54a having the included fluid jet emanator 56a extend along and within the lumen 174 of the distal spiral metal tube 144. The fluid jet emanator 56a at the distal end of the distal high pressure tube 54a is located and secured distally in the lumen 174 of the distal spiral metal tube 144 just distal of the inflow orifices 158a-158n, as shown in FIG. 20. The outer arcuate perimeter of the fluid jet emanator 56a is suitably secured, such as by, but not limited to, a weldment to the inner diameter of the distal spiral metal tube 144, thereby fixing the fluid jet emanator 56a to the distal spiral metal tube 144 and securing the fluid jet emanator 56a with respect to the outflow orifices 156a-156n and the inflow orifices 158a-158n, (FIG. 20), thereby eliminating the use of a radiopaque marker band or of a support ring as a securing or support device.

The guidewire tube 155 having the lumen 157 is securely accommodated by a crescent-shaped truncated and rounded slot 188 at the formed tubular portion 184 and is secured thereto by an adhesive or other suitable attachment methods, if required, and extends distally from the formed tubular portion 184 at the guidewire tube exit region 154 through an orifice 190 (FIG. 16), where the orifice 190 transitions between the distal end of the truncated and rounded slot 188 and the lumen 172 of the distal spiral metal tube 144. The guidewire tube 155 continues through the arcuate passageway 57a of the fluid jet emanator 56a, and further through the distal portion of the lumen 174 of the spiral metal tube 144 where the distal portion of the guidewire tube 155 terminates securely, such as by heat bonding or other suitable means, within the passageway 196 of the flexible tapered tip 137. Heat can be applied to form the tapered tip 137 of increasingly flexible shape in a distal direction at the end of the catheter tube 124, as well as to engagingly secure the distal end portion of the guidewire tube 155 to and within the tapered tip 137. The tapered tip 137 may also be formed through a cold drawn down process or may be physically attached through adhesives or polymer reintegration.

Figure 16:
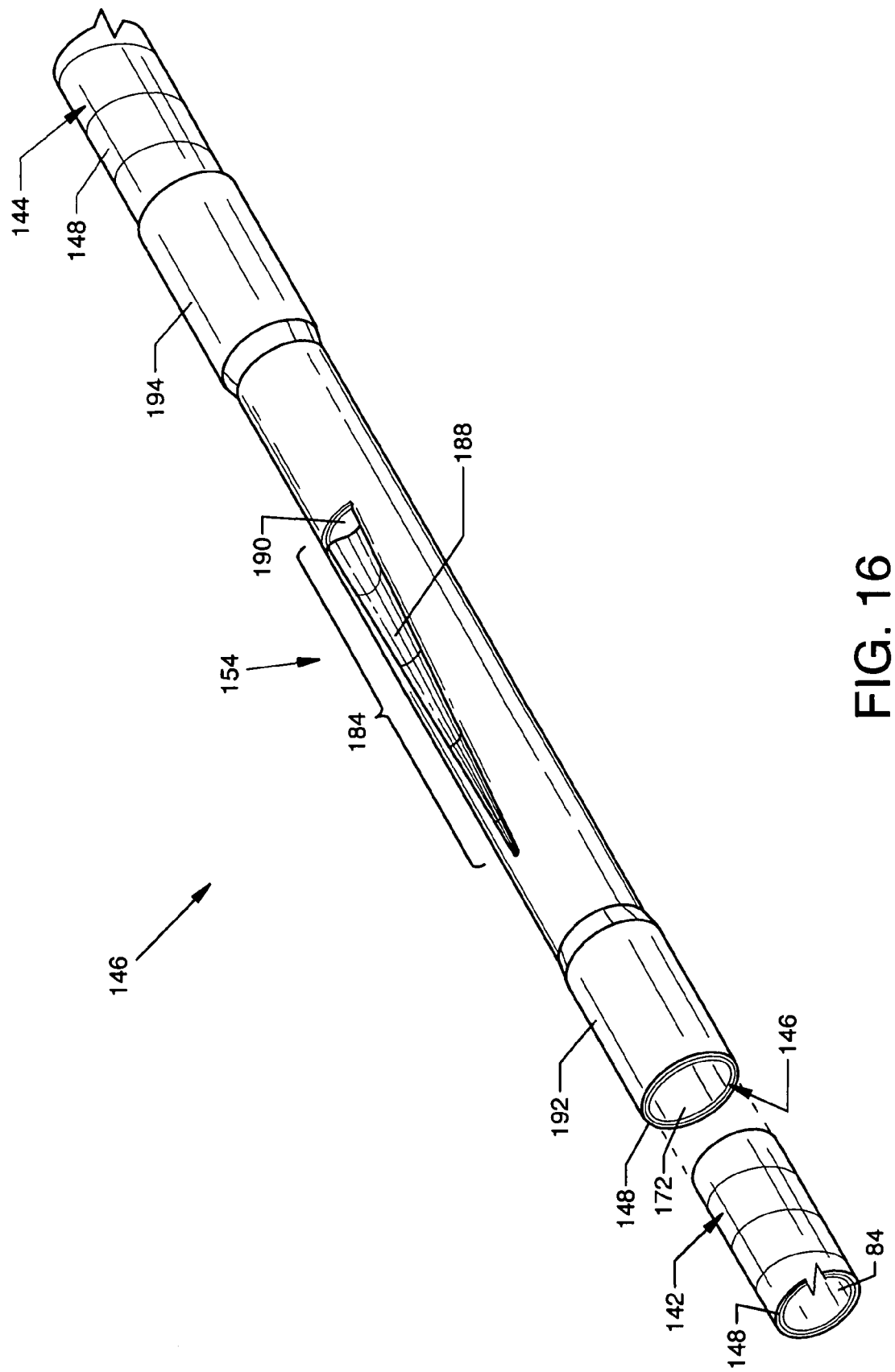
FIG. 16 is an isometric view of the distal end of the intermediate tube in close association with the proximal end of the distal spiral metal tube and of the proximal end of the intermediate tube with the distal end of the proximal spiral metal tube shown distanced from the intermediate tube.
Figure 17:
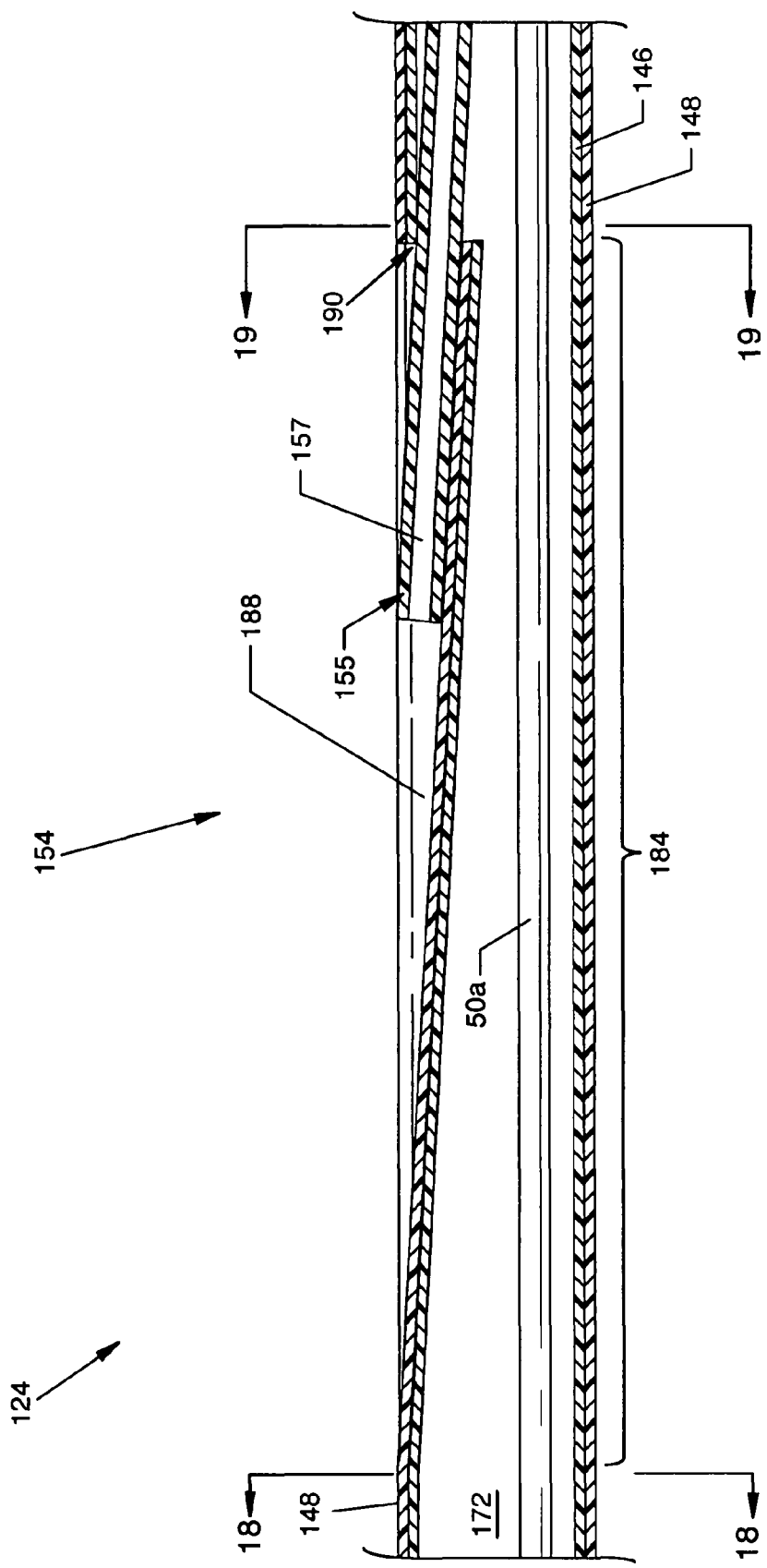
FIG. 17 is a cross section view of the catheter tube along line 17-17 of FIG. 10.

FIG. 16 is an isometric view of the distal end of the intermediate tube 146 in close association with the proximal end of the distal spiral metal tube 144 and of the proximal end of the intermediate tube 146 with the distal end of the proximal spiral metal tube 142 shown distanced from the intermediate tube 146. The intermediate tube 146 includes opposed flared ends 192 and 194 for accommodated connection with the proximal spiral metal tube 142 and with the distal spiral metal tube 144, respectively. Also included is the guidewire tube exit region 154 which is delineated mostly by the formed tubular portion 184 of the intermediate tube 146. The formed tubular portion 184 includes geometry in the form of a truncated and rounded slot 188 of decreasing depth in a proximal direction which accommodates the guidewire tube 155 (FIG. 15). The truncated and rounded slot 188 is substantially formed in the shape of a nearly full semicircular arc at the extreme distal end of the formed tubular portion 184. The arc, while the radius remains constant, is decreased progressing proximally from the extreme distal end of the formed tubular portion 184 to provide for an angled transitional accommodation of the guidewire tube 155, as shown in FIGS. 15 and 17. Other transitional accommodation for routing of the guidewire tube 155 is offered by the orifice 190, previously referenced in connection with FIG. 15. The lumen 172 interior to the intermediate tube 146, depending on component lengths, generally can accommodate a portion of the proximal high pressure tube 50a and also functions as part of the overall effluent exhaust path.

FIG. 17 is a cross section view of the catheter tube 124 along line 17-17 of FIG. 10. Shown in particular is the guidewire tube exit region 154, the formed tubular portion 184, and the proximal end of the guidewire tube 155 at the guidewire tube exit region 154. The proximal end of the guidewire tube 155 is accommodated by the truncated and rounded slot 188 and a portion of the co-located overlying polymer jacket 148 to which it is secured, if required, by an adhesive, by welding, or other such suitable method, and by the orifice 190 at the distal end of the truncated and rounded slot 188. The proximal end of the guidewire tube 155 is of such length that the outer profile of the catheter tube 124 is not exceeded so as to maintain the desired minimal catheter profile. The portion of the truncated and rounded slot 188, which is not occupied by the proximal end of the guidewire tube 155 and which is proximal to the proximal end of the guidewire tube 155, can also be utilized to accommodate a guidewire without structure interference. Also illustrated is the proximal high pressure tube 50a having the lumen 88a (FIGS. 18 and 19) passing through the lumen 172. Lumen 172 of the intermediate tube 146 functions as a portion of the exhaust route extending the length of the catheter tube 124.

Figure 18:
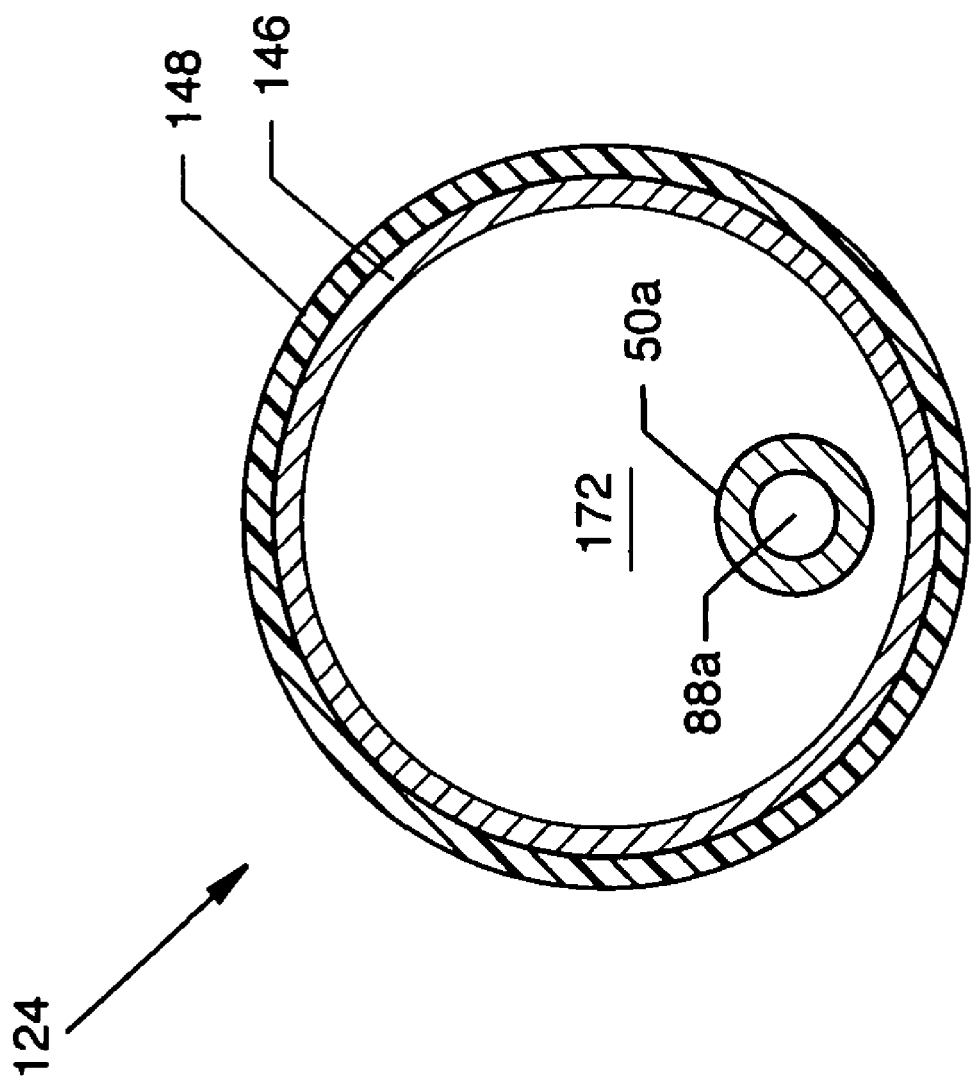
FIG. 18 is a cross section view of the catheter tube along line 18-18 of FIG. 17.

FIG. 18 is a cross section view of the catheter tube 124 along line 18-18 of FIG. 17. Illustrated in particular is the lumen 172 of the intermediate tube 146 which functions as part of the exhaust route through the catheter tube 124 with minimal obstructions or restrictions therein.

Figure 19:
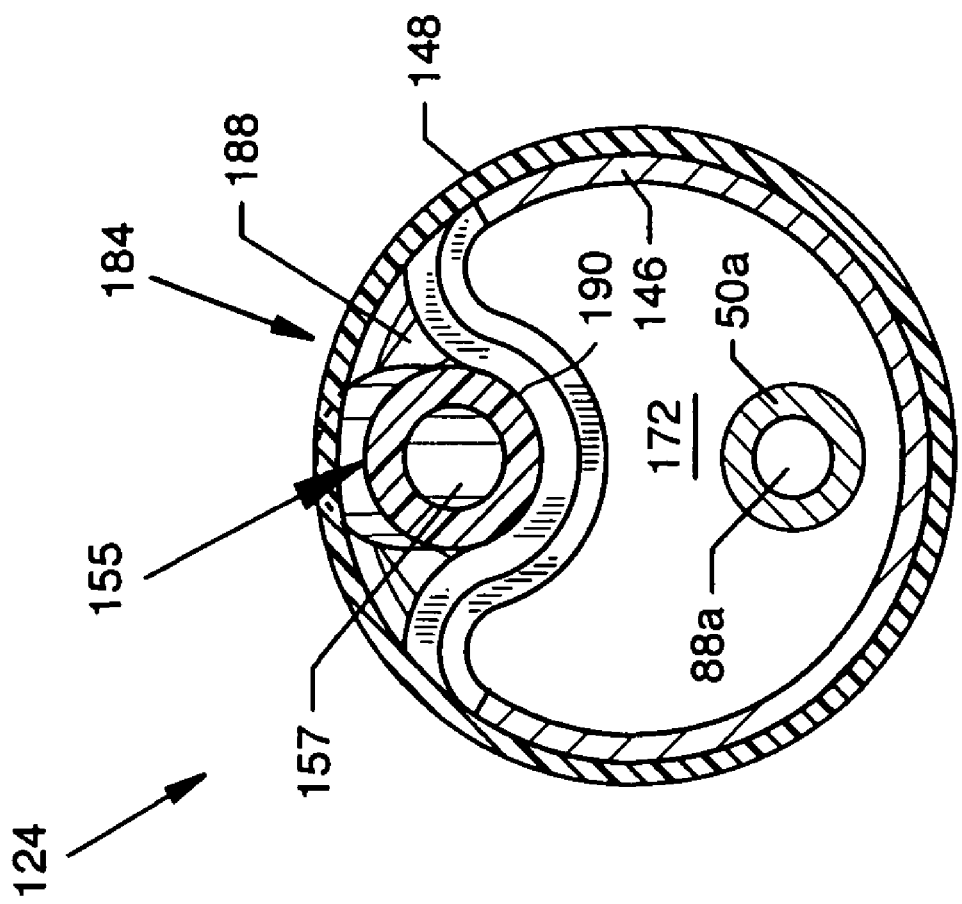
FIG. 19 is a cross section view of the catheter tube along line 19-19 of FIG. 17.
Figure 20:
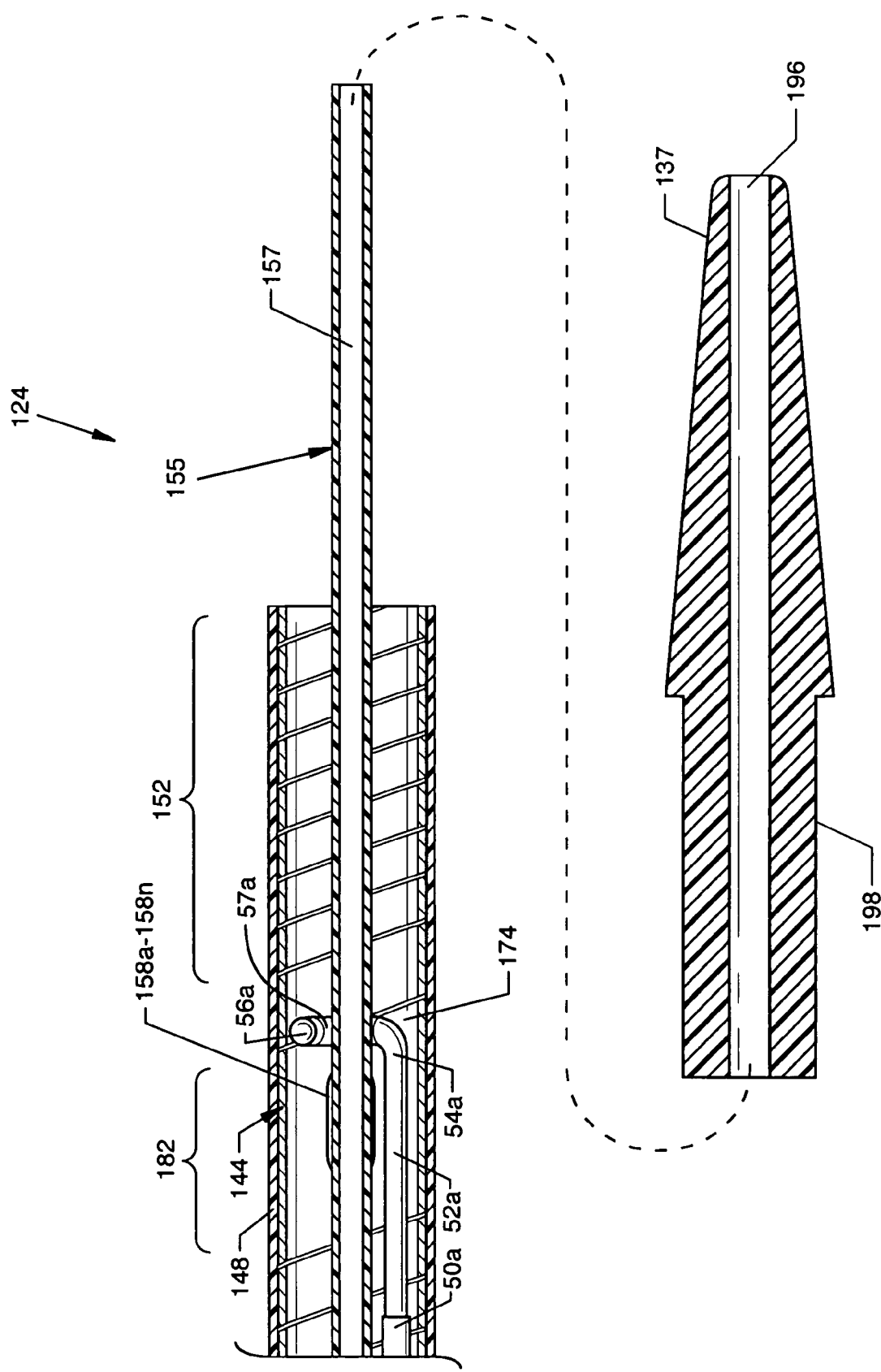
FIG. 20 is a section view along line 20-20 of FIG. 10 of the distal portion of the catheter tube including the tapered tip shown displaced from the catheter tube.

FIG. 19 is a cross section view of the catheter tube 124 along line 19-19 of FIG. 17. Illustrated in particular is the alignment and accommodation of the guidewire tube 155 in the truncated and rounded slot 188 at the formed tubular portion 184 of the intermediate tube 146.

Figure 21:
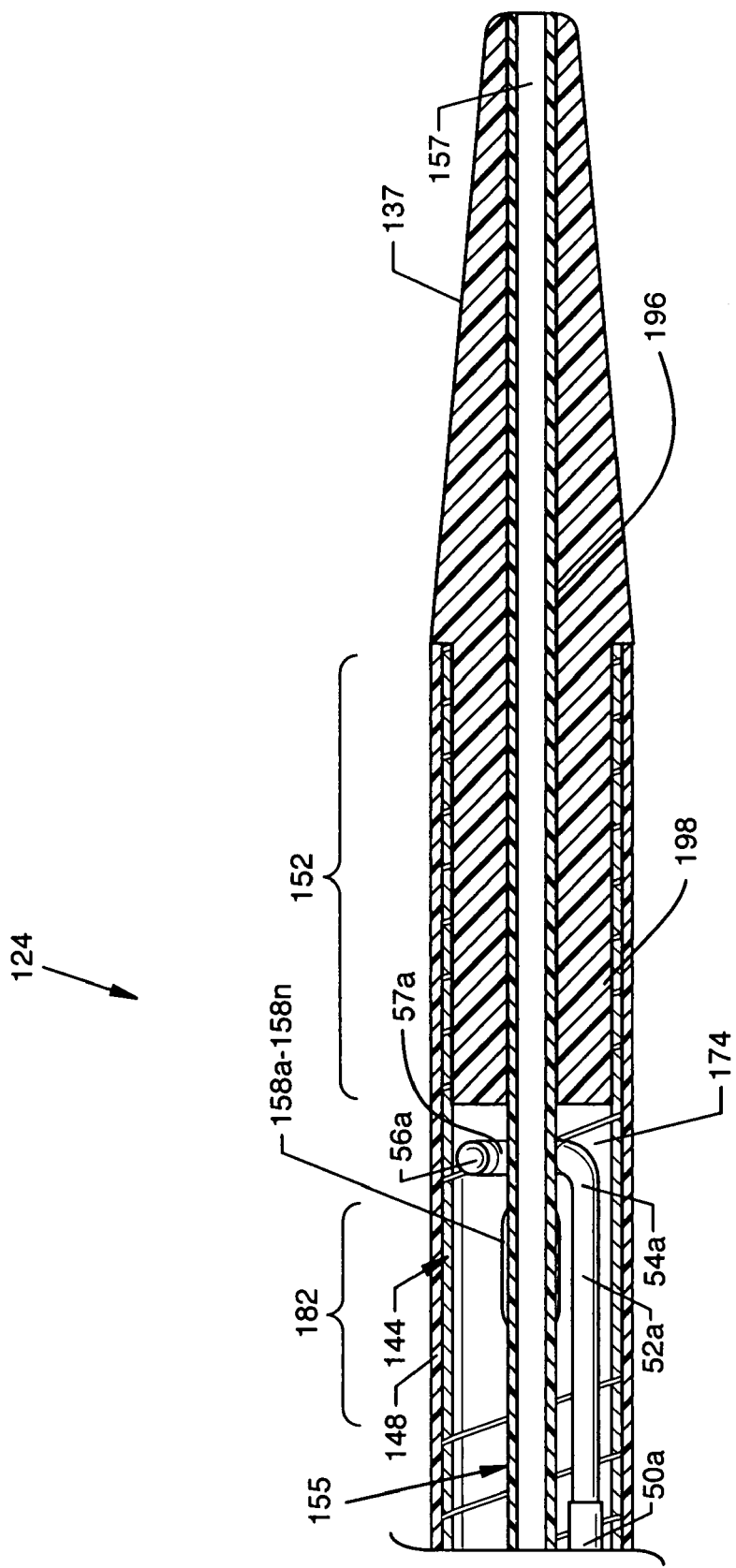
FIG. 21 is the same as FIG. 20 with the tapered tip shown engaging the distal spiral metal tube and the guidewire tube; and, FIGS. 22 and 23 illustrate the mode of operation of one form of the present invention, where

FIG. 20 is a section view of the distal portion of the catheter tube 124 including the tapered tip 137 along line 20-20 of FIG. 10 where the tapered tip 137 is shown removed from the distal spiral metal tube 144, and FIG. 21 is the same as FIG. 20 with the tapered tip 137 shown engaging the distal spiral metal tube 144 and the guidewire tube 155. The radiopaque marker band of the first form of the invention is not included due to the trackability of the metal structure of the catheter tube 124. The outer arcuate semi-perimeter of the fluid jet emanator 56*a* opposing the arcuate passageway 57*a* is suitably secured, such as, but not limited to, a weld directly to the distal interior of the distal spiral metal tube 144 of the catheter tube 124 at a location just distal to the inflow orifices 158*a*-158*n*. The use of a support ring, such as support ring 86, is not required for mounting of the fluid jet emanator 56*a* as the structure of the distal spiral metal tube 144 is sufficiently sturdy enough for mounting. Also, the metal structure of the distal spiral metal tube 144 is of sufficient strength to prevent any deformation or collapsing of the distal spiral metal tube 144 in the region of the inflow orifices 158*a*-158*n* without the use of a support ring. The flexible tapered tip 137 includes a passageway 196 for fixed accommodation of the distal end of the guidewire tube 155 and also includes a reduced constant radius section 198 which is accommodated by and secured within the distal portion of the lumen 174 of the distal spiral metal tube 144.

Structure is provided to nurture and aid introduction of and passage of the distal portion of the catheter tube 124 through blood vessels to the sites of thrombotic deposits or lesions. The flexible tapered tip 137, as opposed to a rounded but nontapered tip, can part and more easily penetrate thrombotic deposits or lesions during insertional travel in a distal direction instead of advancing or pushing such thrombotic deposits or lesions distally. The decreasing diameter in a distal direction of the tapered tip 137 also allows for increasing flexibility to negotiate and pass through tortuous vascular paths. The portion of the catheter tube 124 which immediately follows the tapered tip 137 on a tortuous negotiation and passage is influenced by the supportive structure of the distal spiral metal tube 144 which offers reinforcement to form and contribute to maintaining the diameter of the catheter tube 124 along the entire catheter tube 124 against bending or collapsing due to tortuous paths or negative pressures, especially in the regions in close proximity to or including the inflow orifices 158*a*-158*n* and the outflow orifices 156*a*-156*n*. Such support allows the use of thinner wall dimension for the catheter tube 124 to allow for a larger and more effective and efficiently sized exhaust lumen, i.e., the combination of lumens 170, 172 and 174, as well as contributing to a lesser sized outer diameter. Such support also contributes to supportively maintaining the diameter and overall shape of the catheter tube 124 when it is pushed or advanced along a vein or other vessel, as well as providing torsional support.

Mode of Operation

Figure 22:
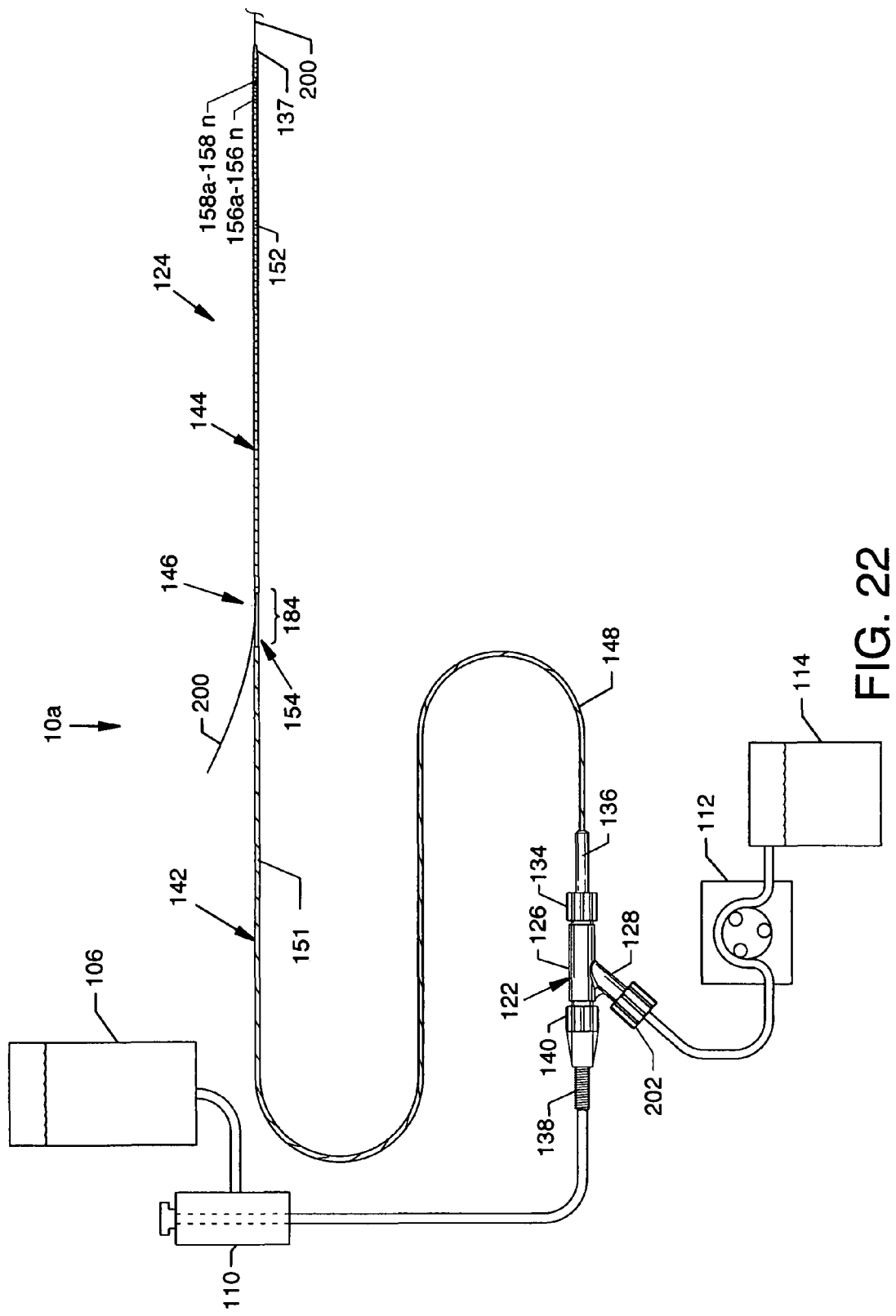
FIG. 22 illustrates the miniature flexible thrombectomy catheter connected to ancillary devices, and where
Figure 23:
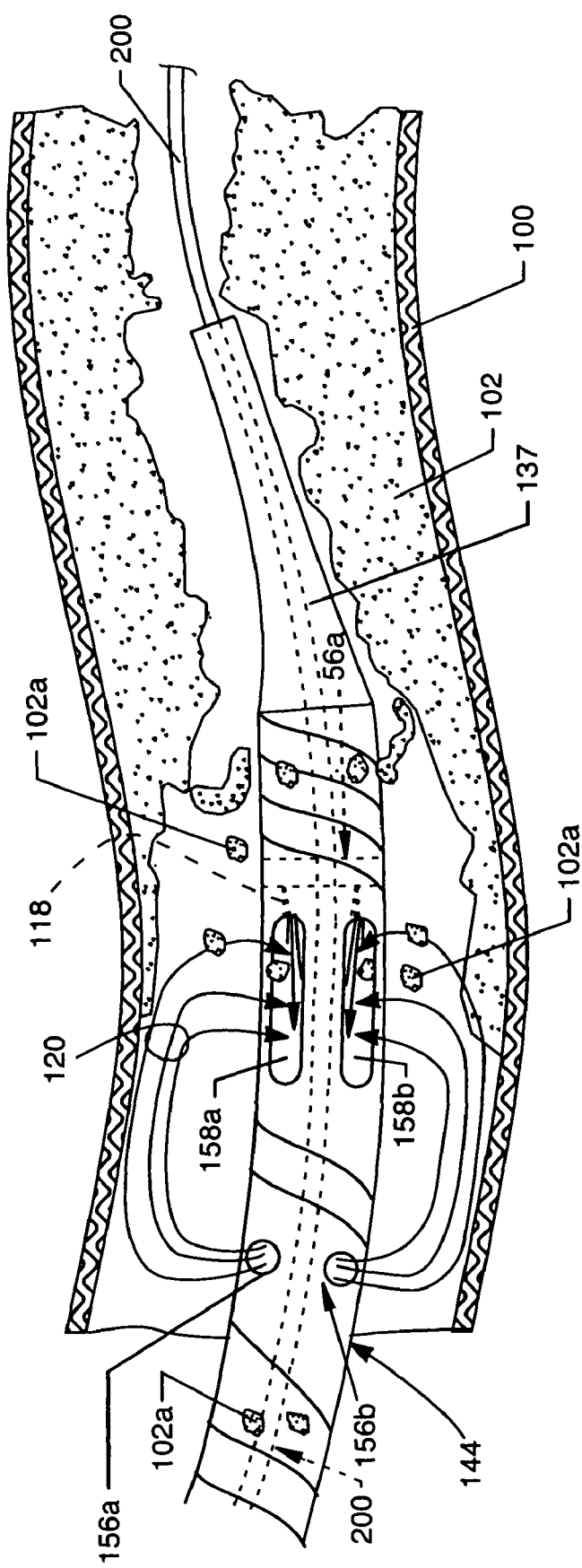
FIG. 23 is a side view of the distal region of the miniature flexible thrombectomy catheter in the performance of the method of use thereof within a small blood vessel.

FIGS. 22 and 23 illustrate the mode of operation of one form of the present invention where FIG. 22 illustrates the miniature flexible thrombectomy catheter 10*a* connected to ancillary devices, and where FIG. 23 illustrates a side view of the distal region of the miniature flexible thrombectomy catheter 10*a* in the performance of the method of use thereof within a small blood vessel 100 (shown in cross section) at a site of a thrombotic deposit or lesion 102. The mode of operation is best understood by referring to FIGS. 22 and 23, as well as previously described figures.

In FIG. 22, the rapid exchange fluid jet thrombectomy device 10*a* is shown engaged over and about a guidewire 200 where the guidewire 200 (previously engaged in the blood vessel 100 of FIG. 23) first engages the lumen 157 of the guidewire tube 155 at the tapered tip 137 of the distal spiral metal tube 144 followed by exiting of the guidewire 200 from the lumen 157 (FIG. 17) at the proximal end of the guidewire tube 155 at the guidewire tube exit region 154. A fluid source 106 and a high pressure fluid pump 110 connect as shown to the manifold 122 via the threaded high pressure connection port 138 by the Luer fitting 140 or optionally by a direct connection. An optional exhaust regulator 112 and a collection chamber 114 connect to the threaded branch end of the exhaust branch 128 of the manifold 122 by a Luer fitting 202, as shown.

FIG. 23 is a side view of the distal portion of the rapid exchange fluid jet thrombectomy device 10*a* in the performance of the method of use thereof, with particular attention given to the distal region of the distal spiral metal tube 144 including the flexible tapered tip 137 positioned in a blood vessel 100 at a site of a thrombotic deposit or lesion 102. Multiple high velocity fluid jet streams 118 of saline, for example, or other suitable fluid, are shown being emitted in a proximal direction from the fluid jet emanator 56*a* to impinge upon and carry away thrombotic deposits or lesions 102. Other fluid jet emanators of appropriate size and/or configuration can be incorporated within the distal portion of the distal spiral metal tube 144 as an alternative to the fluid jet emanator 56*a* illustrated in this figure to emanate or emit one or more high velocity fluid jet streams 118 distally along or near the longitudinal axis of the distal spiral metal tube 144 to accomplish the same purpose as that described for the fluid jet emanator 56*a*. The high velocity fluid jet streams 118 of saline pass outwardly through the outflow orifices 156*a*-156*n* in a radial direction creating cross stream jets 120 (lower velocity jets) directed outwardly toward the wall of the blood vessel 100 and are influenced by the low pressure at the inflow orifices 158*a*-158*n* to cause the cross stream jets 120 to flow circumferentially and distally to impinge on, provide drag forces on, and break up thrombotic deposits or lesions 102 and to, by entrainment, urge and carry along the particles 102*a* of thrombotic deposits or lesions 102 through the inflow orifices 158*a*-158*n*, a relatively low pressure region, into the high velocity fluid jet streams 118 where the thrombus is further macerated into microscopic particles, and then into the lumen 174 of the distal spiral metal tube 144 (FIG. 20). A certain portion of this macerated debris which is mixed with fresh saline is removed through the lumen 174 of the distal spiral metal tube 144 and a certain portion flows back out the outflow orifices 156*a*-156*n* and recirculates to break up more debris which is returned to the inflow orifices 158*a*-158*n*. In this way, much more fluid flow circulates through the system than is injected through the jet orifices 94*a*-94*n* (FIG. 7) of the fluid jet emanator 56*a*. For purposes of illustration and example, three to ten times more flow circulates through the system than is delivered by the jet orifices 94*a*-94*n*. The entrainment through the inflow orifices 158*a*-158*n* is based on entrainment by the high velocity fluid jet streams 118. The outflow is driven by internal pressure which is created by the high velocity fluid jet streams 118 and the fluid entrained through the inflow orifices 158*a*-158*n*. Enhanced clot removal is attainable because of the recirculation pattern established between outflow and inflow orifices 156*a*-156*n* and 158*a*-158*n*, which creates a flow field that maximizes drag force on wall-adhered thrombus. Since the entrained thrombus is macerated into microscopic particles, those particles that exit the outflow orifices 156*a*-156*n* are not of sufficient size to significantly block the distal circulation, and will be re-entrained into the inflow orifices 158*a*-158*n* at a high rate. In a no-flow situation or when flow is stopped with another device, such as an occlusive balloon, material can be recirculated and rediluted until all that remains is saline and all particles are removed.

Various modifications can be made to the present invention without departing from the apparent scope thereof.

PARTS LIST 10 miniature flexible thrombectomy catheter
10a miniature flexible thrombectomy catheter
12 manifold
14 catheter tube
16 central tubular body
18 threaded exhaust branch
20 high pressure connection branch
22 cavity body
24 threaded connection port
26 Luer fitting
28 strain relief tube
30 proximal tube
32 distal tube
32a proximal section (of 32)
32b distal section (of 32)
34 flexible tip
36a-n outflow orifices
38a-n inflow orifices
40 marker band
41 market band
42 hemostasis nut
43 support ring
44 threaded high pressure connector port
46 Luer connector
48 introducer
50 proximal high pressure tube
50a proximal high pressure tube
52 nitinol tube
52a nitinol tube
54 distal high pressure tube
54a distal high pressure tube
56 fluid jet emanator
56a fluid jet emanator
57 arcuate passageway
57a arcuate passageway
58 jet body
58a jet body
60 high pressure connection branch passageway
62 exhaust branch passageway
64 tapered central passageway
66 cavity
68 threads
69 threads
70 self-sealing hemostasis valve
72 washer
74 cylindrical boss
76 ferrule
78 passageway
80 interior passageway
82 lumen (of proximal section 32a)
84 lumen (of distal section 32b)
84a narrow section (of lumen 84)
86 support ring
88 lumen (of proximal high pressure tube 50)
88a lumen (of proximal high pressure tube 50a)
90 lumen (of nitinol tube 52)
90a lumen (of nitinol tube 52a)
92 lumen (of distal high pressure tube 54)
92a lumen (of distal high pressure tube 54a)
94a-n jet orifices
96 joint
96a joint
98 joint
98a joint
100 blood vessel
102 thrombotic deposit or lesion
102a particles
104 guidewire
106 high pressure fluid source
108 Luer fitting
110 high pressure fluid pump
112 exhaust regulator
114 collection chamber
116 Luer fitting
118 high velocity fluid jet stream
120 cross stream jets
122 manifold
124 catheter tube
126 central tubular body
128 threaded exhaust branch
130 threaded connection port
132 threaded connection port
134 Luer fitting
136 strain relief tube
137 tapered tip
138 threaded high pressure connection port
140 Luer fitting
142 proximal spiral metal tube
144 distal spiral metal tube
146 intermediate tube
148 polymer jacket
150 wide pitch
151 medium pitch
152 close pitch
154 guidewire tube exit region
155 guidewire tube
156a-n outflow orifices
157 lumen (of guidewire tube 155)
158a-n inflow orifices
162 central passageway
164 exhaust branch passageway
166 ferrule
168 passageway
170 lumen (of proximal spiral metal tube 142)
172 lumen (of intermediate tube 146)
174 lumen (of distal spiral metal tube 144)
176 proximal spiral cut
178 distal spiral cut
180 wide pitch region
182 wide pitch region
184 formed tubular portion
188 truncated and rounded slot
190 orifice.
192 flared end
194 flared end
196 passageway
198 reduced constant radius section
200 guidewire
202 Luer fitting

The invention claimed is:

1. A thrombectomy catheter device for use in treating neurological anatomy comprising a manifold having a main body with a longitudinal axis, said main body having an upstream end and a downstream end, a liquid input port connected to said upstream end of said main body, an exhaust branch connected to said main body near said upstream end of said main body, and an elongated flexible catheter connected to said downstream end of said main body, said flexible catheter having a distal end and an internal high pressure tube for receiving and transmitting therethrough a liquid from said input port, said internal high pressure tube having a fluid jet emanator at a downstream end thereof said fluid jet emanator has a downstream termination in the form of a semi-loop in an arc of about 160 degrees and said flexible catheter having spaced output and input orifices upstream from said fluid jet emanator wherein said internal high pressure tube comprises successive flexible sections made from stainless steel, nitinol, and stainless steel whereby a nitinol to stainless steel bond is formed near the downstream end, said bond being formed via laser swaging with gold plating and said distal end of said flexible catheter has a diameter of about 3 French.

2. The catheter device of claim 1, wherein said fluid jet emanator has several jet orifices therein.

3. The catheter device of claim 1, wherein several jet orifices are located in said semi-loop of said fluid jet emanator.

4. The catheter device of claim 1, wherein said input orifices are adjacent said fluid jet emanator and said output orifices are upstream from and in close proximity to said input orifices.

5. The catheter device of claim 1, wherein said flexible catheter has a downstream end with a tapered tip.

6. The catheter device of claim 1, wherein a flexible guidewire extends internally through said main body from said upstream end of said main body along said longitudinal axis to said downstream end of said main body and then internally through said flexible catheter and exiting out from said tapered tip of said flexible catheter.

7. The catheter device of claim 1, wherein said elongated flexible catheter is made from several flexible sections, mainly a proximal section and a distal section.

8. The catheter device of claim 7, wherein said proximal section is made from a thermoplastic elastomer and said distal section is made from a braided polyimide.

9. The catheter of claim 7, wherein said distal section has a smaller diameter than said proximal section.

10. A catheter system comprising the catheter device of claim 1 and a liquid source connected via a high pressure pump to said liquid input port of said main body and a collection chamber connected to said exhaust branch of said main body.

11. The catheter system of claim 10, further comprising an exhaust regulator connected between said collection chamber and said exhaust branch.

12. The catheter of claim 1, further comprising a guidewire tube and an intermediate tube accommodating the guidewire tube, said intermediate tube being located along the elongated flexible catheter, so that a guidewire can pass through the guidewire tube and into and through the distal end of the elongated flexible catheter.

13. The catheter of claim 1, wherein the elongated flexible catheter comprises a metal spiral and a polymer jacket.

14. The catheter of claim 13, wherein said metal spiral has regions of differing pitch.

15. The catheter device of claim 1, wherein the successive flexible sections of the internal high pressure tube have a smaller diameter than the previous section to which it is attached.

16. A thrombectomy catheter device for use in treating neurological anatomy comprising a manifold having a main body with a longitudinal axis, said main body having an upstream end and a downstream end, a liquid input port connected to said upstream end of said main body, an exhaust branch connected to said main body near said upstream end of said main body, and an elongated flexible catheter connected to said downstream end of said main body, said flexible catheter having a distal end and an internal high pressure tube for receiving and transmitting therethrough a liquid from said input port, said internal high pressure tube having a fluid jet emanator at a downstream end thereof said fluid jet emanator has a downstream termination in the form of a semi-loop in an arc of about 160 degrees and said flexible catheter having spaced output and input orifices upstream from said fluid jet emanator, wherein said internal high pressure tube comprises successive flexible sections made from stainless steel, nitinol, and stainless steel whereby a nitinol to stainless steel bond is formed near the downstream end, said bond being formed via laser swaging with gold plating and each successive flexible section has a smaller diameter than the previous section to which it is overlapingly attached.

17. A jet body for a thrombectomy catheter device for use in treating neurological anatomy wherein the jet body comprises at least three components formed of at least two dissimilar metals, the at least three components comprising a plurality of metal tubular sections and a metal fluid jet emanator said fluid jet emanator has a downstream termination in the form of a semi-loop in an arc of about 160 degrees, wherein at least one of the metal tubular sections has a metallic plating applied and is laser swaged to at least one other component of dissimilar metal so that the applied metallic plating provides a barrier to inhibit mixing of the dissimilar metals and said jet body has a diameter of less than 3 French.

18. The jet body of claim 17, wherein the at least two dissimilar metals comprise stainless steel and nitinol.

19. The jet body of claim 17, wherein the metallic plating comprises gold.

20. The jet body of claim 18, wherein the fluid jet emanator comprises stainless steel, and at least a portion of the stainless steel of the fluid jet emanator is plated with gold and swaged to a nitinol tubular section.

21. The jet body of claim 20, wherein the fluid jet emanator comprises stainless steel tubing.

22. The jet body of claim 17, wherein the at least three components are joined to form a high strength elongated tubular assembly for passage of high pressure fluid along the length thereof to supply the high pressure fluid to the fluid jet emanator.

* * * * *

UNITED STATES PATENT AND TRADEMARK OFFICE
CERTIFICATE OF CORRECTION

Page 1 of 2

PATENT NO. : 8,012,117 B2
APPLICATION NO. : 11/702990
DATED : September 6, 2011
INVENTOR(S) : Bonnette et al.

It is certified that error appears in the above-identified patent and that said Letters Patent is hereby corrected as shown below:

In Column 23, Lines 6-7, Claim 1, delete "said fluid jet emanator has a downstream termination" and insert -- said fluid jet emanator having a downstream termination --, therefor.

In Column 23, Lines 14-15, Claim 1, delete "and said distal end of said flexible catheter has a diameter" and insert -- and said distal end of said flexible catheter having a diameter --, therefor.

In Column 23, Line 26, Claim 6, delete "The catheter device of claim 1, wherein" and insert -- "The catheter device of claim 5, wherein --, therefor.

In Column 23, Line 38, Claim 9, delete "The catheter of claim 7" and insert -- The catheter device of claim 7 --, therefor.

In Column 23, Line 48, Claim 12, delete "The catheter of claim 1,", and insert -- The catheter device of claim 1," --, therefor.

In Column 23, Line 49, in Claim 12, after "catheter" insert -- device --, therefor.

In Column 23, Line 54, Claim 13, delete "The catheter of claim 1," and insert -- The catheter device of claim 1, --, therefor.

In Column 23, Line 55, in Claim 13, after "catheter" insert -- device --, therefor.

In Column 24, Line 1, in Claim 14, after "catheter" insert -- device --, therefor.

In Column 24, Lines 18-19, Claim 16, delete "said fluid jet emanator has a downstream termination" and insert -- said fluid jet emanator having a downstream termination --, therefor.

In Column 24, Lines 26-27, Claim 16, delete "and each successive flexible section has a smaller diameter" and insert -- and each successive flexible section having a smaller diameter --, therefor.

Signed and Sealed this
Eighteenth Day of September, 2012

David J. Kappos
*Director of the United States Patent and Trademark Office*

CERTIFICATE OF CORRECTION (continued)
U.S. Pat. No. 8,012,117 B2

In Column 24, Line 28, in Claim 16, delete "overlapingly" and insert -- overlappingly --, therefor.

In Column 24, Line 24, Claim 17, delete "said fluid jet emanator has a downstream termination" and insert -- said fluid jet emanator having a downstream termination --, therefor.